(12) United States Patent
Paudel et al.

(10) Patent No.: US 12,048,650 B2
(45) Date of Patent: Jul. 30, 2024

(54) SYSTEM AND METHOD OF DETERMINING INCISION DEPTHS IN EYES

(71) Applicant: ALCON INC., Fribourg (CH)

(72) Inventors: Arun Paudel, Berlin (DE); Olaf Kittelmann, Berlin (DE); Matthias Foesel, Memmelsdorf (DE)

(73) Assignee: ALCON INC., Fribourg (CH)

( * ) Notice: Subject to any disclaimer, the term of this patent is extended or adjusted under 35 U.S.C. 154(b) by 0 days.

(21) Appl. No.: 18/451,316

(22) Filed: Aug. 17, 2023

(65) Prior Publication Data

US 2023/0390113 A1 Dec. 7, 2023

Related U.S. Application Data

(63) Continuation of application No. 17/119,863, filed on Dec. 11, 2020, now Pat. No. 11,759,359.

(60) Provisional application No. 62/947,735, filed on Dec. 13, 2019.

(51) Int. Cl.
   *A61B 3/10* (2006.01)
   *A61F 9/008* (2006.01)

(52) U.S. Cl.
   CPC ........ *A61F 9/00802* (2013.01); *A61B 3/1005* (2013.01); *A61B 3/1025* (2013.01); *A61F 2009/00878* (2013.01); *A61F 2009/00897* (2013.01)

(58) Field of Classification Search
   CPC .. A61F 9/00802; A61F 9/008; A61F 9/00804; A61F 9/00827; A61F 2009/00878; A61F 2009/00897; A61F 2009/00844; A61F 2009/00872; A61B 3/1005; A61B 3/1025; A61B 3/102; A61B 3/13
   USPC ............................................. 606/4; 351/206
   See application file for complete search history.

(56) References Cited

U.S. PATENT DOCUMENTS

| | | | |
|---|---|---|---|
| 10,736,779 B2 * | 8/2020 | Schuele | A61F 9/00812 |
| 10,973,683 B2 * | 4/2021 | Schuele | A61F 9/00825 |
| 11,229,357 B2 * | 1/2022 | Schuele | A61B 3/1173 |
| 11,478,380 B2 * | 10/2022 | Schuele | A61F 9/008 |
| 11,759,359 B2 * | 9/2023 | Paudel | A61B 3/1005 |
| | | | 606/4 |
| 2015/0335478 A1 * | 11/2015 | Cherkas | A61F 9/008 |
| | | | 606/5 |
| 2016/0235588 A1 * | 8/2016 | Hart | A61B 3/1173 |
| 2018/0110652 A1 * | 4/2018 | Schuele | A61F 9/008 |
| 2018/0214305 A1 * | 8/2018 | Schuele | A61F 9/00825 |

(Continued)

*Primary Examiner* — William R Alexander

(57) ABSTRACT

The disclosure provides a system that may: determine first multiple focal point distances associated with respective multiple positions of a plane orthogonal to a laser beam; determine second multiple focal point distances associated with the respective multiple positions via for each position of the multiple positions: determine multiple intensity values associated with respective multiple interim focal point distances, each interim focal point distance greater than each focal point distance of the first multiple focal point distances associated with the position; determine an interim focal point distance respectively associated with a maximum intensity value; and determine a focal point distance as the interim focal point distance; and determine a depth of at least one incision in an eye based at least on differences between each of the second multiple focal point distances and each respective one of the first multiple focal point distances.

15 Claims, 38 Drawing Sheets

(56) References Cited

U.S. PATENT DOCUMENTS

2019/0076017 A1* 3/2019 Schuele .................. A61B 3/14
2020/0360187 A1* 11/2020 Schuele ................. A61F 9/008
2021/0177658 A1* 6/2021 Paudel ................. A61B 3/1005
2021/0361485 A1* 11/2021 Schuele .............. A61F 9/00825

* cited by examiner

SYSTEM AND METHOD OF DETERMINING INCISION DEPTHS IN EYES

BACKGROUND

Field of the Disclosure

This disclosure relates to determining incision depths in eyes.

Description of the Related Art

In the past, optical topography measuring instruments were available. These instruments utilized "white light" interferometry. For example, these instruments are utilized to measure height variations (e.g., surface roughness) of a surface. Interference optical profiling can use wave properties of light to compare an optical path difference between a test surface and a reference surface. For example, a light beam can be split. Half of the beam of light can be reflected from a test material. The other half of the beam of light can be reflected from a reference mirror. Constructive and destructive interference can occur when the two halves of the light beam are combined where respective lengths of the two halves are different. For example, interference fringes (e.g., light and dark bands) can be created. A digital camera can receive the combination of the two halves. Constructive interference can be lighter areas, while destructive interference can be darker areas. For a known wavelength of light, height differences across a surface can be determined in fractions of a wavelength of the light. Based on the height differences, a surface measurement can be determined. For example, a three-dimensional surface map can be determined based on the height differences.

Furthermore, in the past, traditional optical techniques that utilize a one-photon absorption process have limited uses to near surfaces of biological material (e.g., less than one hundred micrometers (100 μm)) for high-resolution imaging. Going deeper into biological material, light scatters and blurs the imaging.

SUMMARY

The present disclosure provides a medical system that may produce a laser beam and may determine first multiple focal point distances associated with respective multiple positions of a plane orthogonal to the laser beam. In one example, the laser beam may include photons associated with multiple frequencies. In another example, the plane may be associated with a X-axis and a Y-axis. The medical system may further determine second multiple focal point distances associated with the respective multiple positions of the plane orthogonal to the laser beam.

To determine second multiple focal point distances associated with the respective multiple positions of the plane orthogonal to the laser beam, the medical system may further, via for each position of the multiple positions: adjust at least one mirror to target the laser beam to the position; determine multiple intensity values associated with respective multiple interim focal point distances, each interim focal point distance greater than each focal point distance of the first multiple focal point distances associated with the position of the multiple positions; determine a maximum intensity value of the multiple intensity values; determine an interim focal point distance of the multiple interim focal point distances respectively associated with the maximum intensity value; and determine a focal point distance of the multiple focal point distances as the interim focal point distance of the multiple interim focal point distances respectively associated with the maximum intensity value. The medical system may further determine a depth of at least one incision in the eye of the patient based at least on differences between each of the second multiple focal point distances and each respective one of the first multiple focal point distances.

To determine multiple intensity values associated with respective multiple interim focal point distances, each interim focal point distance greater than each focal point distance of the first multiple focal point distances associated with the position of the multiple positions, the medical system may further, for each interim focal point distance of the multiple interim focal point distances: adjust a beam expander to focus the laser beam to the interim focal point distance; receive, via the TPA detector, at least a portion of the laser beam reflected from an incision in an eye of a patient; and determine, from the at least the portion of the laser beam, an intensity value of the multiple intensity values associated with the interim focal point distance. The medical system may further determine a topography of the at least one incision in the eye of the patient based at least on differences between each of the second multiple focal point distances and each respective one of the first multiple focal point distances.

To produce the laser beam, the medical system may pulse the laser beam. For example, the medical system may pulse the laser beam at femtosecond pulse durations. The medical system may include an analog to digital converter (ADC). For example, to determine, from the at least the portion of the laser beam, the intensity value of the multiple intensity values associated with the interim focal point distance, the medical system may further receive, by the ADC, an analog signal from the TPA detector; and convert, by the ADC, the analog signal from the TPA detector to the intensity value of the multiple intensity values associated with the interim focal point distance. In one example, the ADC may be configured to convert current into digital values. In another example, the ADC may be configured to convert voltage into digital values.

The present disclosure further includes a non-transient computer-readable memory device with instructions that, when executed by a processor of a medical system, cause the system to perform the above steps. The present disclosure further includes a medical system or a non-transient computer-readable memory device as described above with one or more of the following features, which may be used in combination with one another unless clearly mutually exclusive: i) produce the laser beam; ii) determine first multiple focal point distances associated with respective multiple positions of a plane orthogonal to the laser beam; iii) determine second multiple focal point distances associated with the respective multiple positions of the plane orthogonal to the laser beam via for each position of the multiple positions: a) adjust at least one mirror to target the laser beam to the position; b) determine multiple intensity values associated with respective multiple interim focal point distances, each interim focal point distance greater than each focal point distance of the first multiple focal point distances associated with the position of the multiple positions, via for each interim focal point distance of the multiple interim focal point distances: 1) adjust a beam expander to focus the laser beam to the interim focal point distance; 2) receive, via the TPA detector, at least a portion of the laser beam reflected from an incision in an eye of a patient; and 3) determine, from the at least the portion of the laser beam, an intensity value of the multiple intensity values associated with the interim focal point distance; c) determine a maximum intensity value of the multiple intensity values; d) determine an interim focal point distance of the multiple interim focal point distances respectively associated with the maximum intensity value; and e) determine a focal point distance of the multiple focal point distances as the interim focal point distance of the multiple interim focal point distances respectively associated with the maximum intensity value; iv) determine a depth of at least one incision in the eye of the patient based at least on differences between each of the second multiple focal point distances and each respective one of the first multiple focal point distances; and v) determine a topography of the at least one incision in the eye of the patient based at least on differences between each of the second multiple focal point distances and each respective one of the first multiple focal point distances.

Any of the above systems may be able to perform any of the above methods and any of the above non-transient computer-readable memory devices may be able to cause a system to perform any of the above methods. Any of the above methods may be implemented on any of the above systems or using any of the above non-transient computer-readable memory devices.

It is to be understood that both the foregoing general description and the following detailed description are examples and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

For a more complete understanding of the present disclosure and its features and advantages, reference is now made to the following description, taken in conjunction with the accompanying drawings, which are not drawn to scale, and in which.

DETAILED DESCRIPTION

Figure 1A:
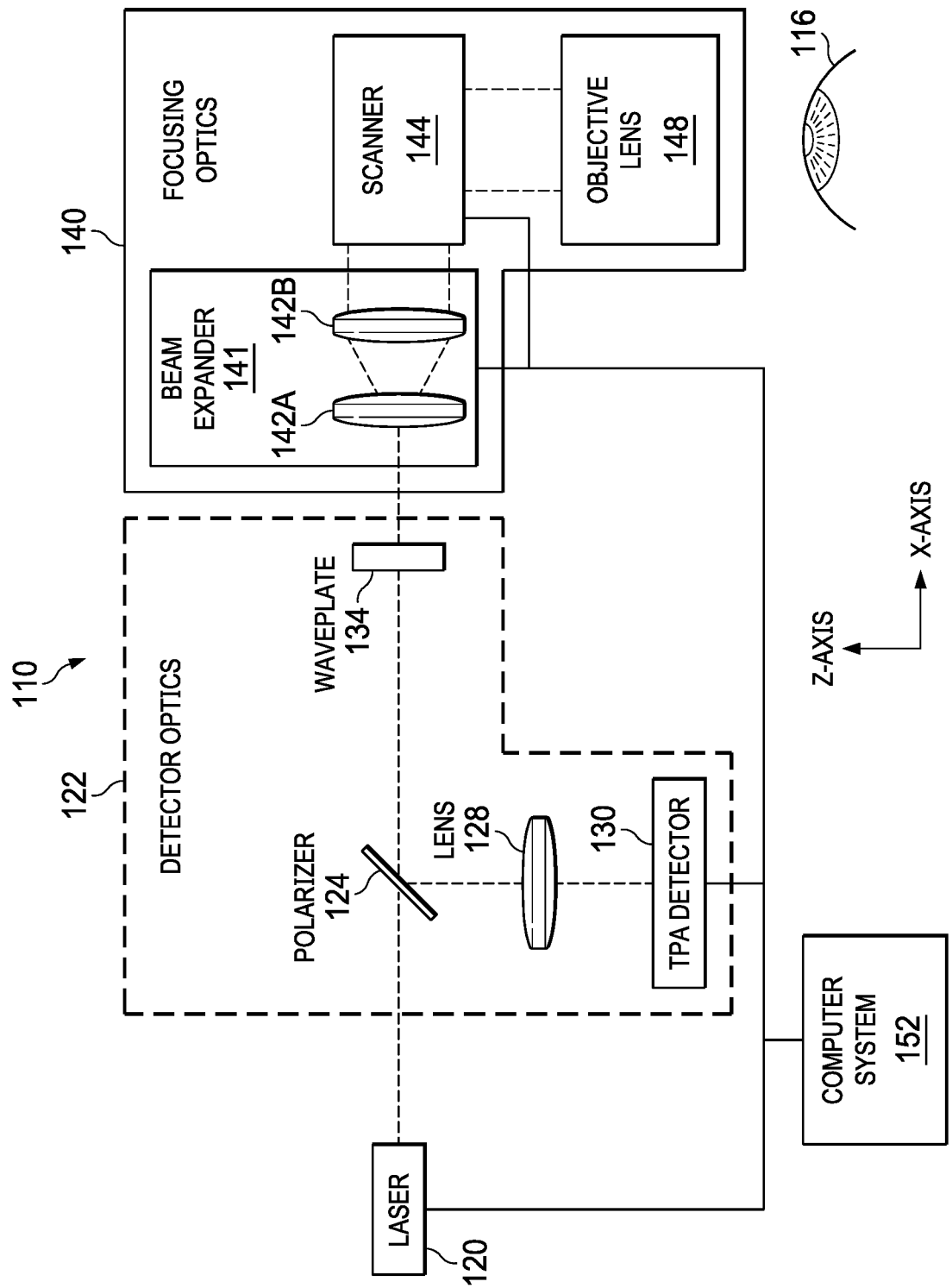
FIG. 1A illustrates an example of an optical system.

In the following description, details are set forth by way of example to facilitate discussion of the disclosed subject matter. It should be apparent to a person of ordinary skill in the field, however, that the disclosed embodiments are examples and not exhaustive of all possible embodiments.

As used herein, a reference numeral refers to a class or type of entity, and any letter following such reference numeral refers to a specific instance of a particular entity of that class or type. Thus, for example, a hypothetical entity referenced by '12A' may refer to a particular instance of a particular class/type, and the reference '12' may refer to a collection of instances belonging to that particular class/type or any one instance of that class/type in general.

Medical systems may be utilized in performing medical procedures with patients. Medical systems may include optics. For example, a medical system may include one or more optical systems that may include optics. An optical system may include one or more optical devices. For example, an optical device may be or may include a device that controls light (e.g., reflects light, refracts light, filters light, transmits light, polarizes light, etc.). An optical device may be made of any material that controls the light as designed. For example, the material may include one or more of glass, crystal, metal, and semiconductor, among others. Examples of optical devices may include one or more of lenses, mirrors, prisms, optical filters, waveguides, waveplates, beam expanders, beam collimators, beam splitters, gratings, and polarizers, among others.

An optical system may be utilized to determine a topography of at least a portion of a patient. For example, an optical system may be utilized to determine a topography of at least a portion of an eye of a patient. The topography of the at least the portion of the eye of the patient may reveal one or more deformations of the at least the portion of the eye of the patient. The topography of the at least the portion of the eye of the patient may reveal damage of the at least the portion of the eye of the patient.

The optical system may include one or more of a laser and a two-photon absorption (TPA) detector, among others. In one example, the laser may produce a laser beam that includes photons of multiple frequencies. In another example, the laser may produce a pulsed laser beam. The pulsed laser beam may include photons of multiple frequencies.

An optical system may be configured to vary focal point distances of a laser beam. A TPA detector may determine an intensity of a reflection of at least a portion the laser beam. In one example, the optical system may determine multiple focal point distances associated with respective multiple positions of a plane orthogonal to the laser beam. The optical system may determine a topography of an eye of a patient based at least on the multiple focal point distances associated with the respective multiple positions. In another example, the optical system may determine first multiple focal point distances associated with respective multiple positions of a plane orthogonal to the laser beam. The optical system may determine second multiple focal point distances associated with the respective multiple positions of the plane orthogonal to the laser beam. The optical system may determine a depth of at least one incision in the eye of the patient based at least on differences between each of the second multiple focal point distances and each respective one of the first multiple focal point distances.

The optical system may be utilized in correcting a cutting depth of an incision based at least on a depth of the incision in an eye of a patient. In one example, the optical system may be utilized to maintain a cutting depth (e.g., without one or more deviations from a prescribed cutting depth) while an incision in the eye of the patient is being performed. In a second example, the optical system may be utilized to maintain a cutting contour (e.g., without one or more deviations from a prescribed cutting depth) while an incision in the eye of the patient is being performed. In a third example, the optical system may be utilized in incising a flap in the eye of the patient with little deviation or no deviation from a prescribed cutting depth. In another example, the optical system may be utilized in incising a lenticule in the eye of the patient with little deviation or no deviation from a prescribed cutting depth. As one example, a WAVELIGHT® FS 200 laser system, available from Alcon Vision LLC, may perform an incision in the eye of the patient. As another example, surgical tooling equipment (e.g., a scalpel, a blade, etc.) may be utilized in performing an incision in the eye of the patient.

Figure 1B:
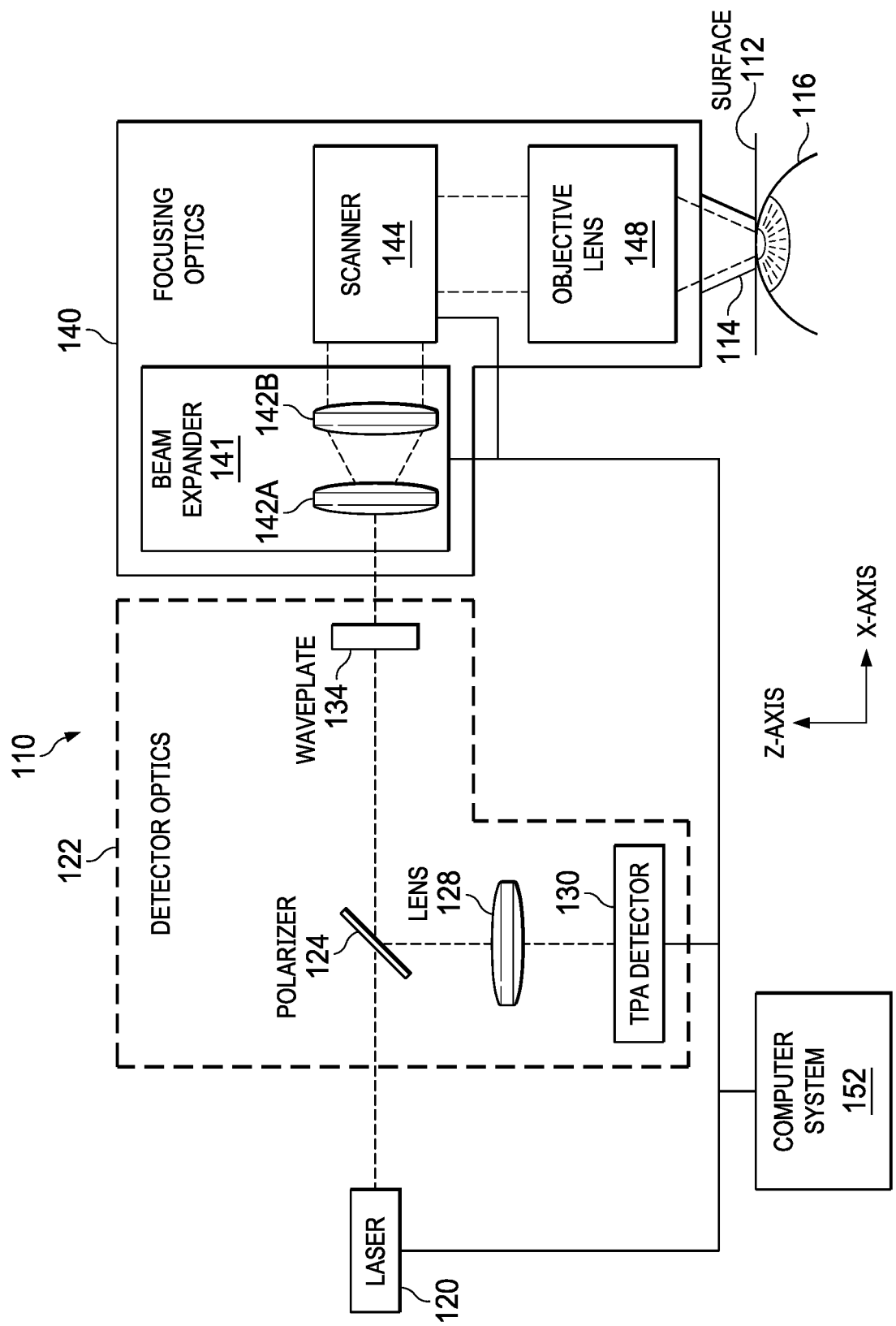
FIG. 1B illustrates another example of an optical system.

Turning now to FIGS. 1A and 1B, an example of an optical system is illustrated. An optical system 110 may be utilized to determine a surface of an eye 116 of a patient. For example, optical system 110 may be utilized to determine a topography of eye 116. Optical system 110 may be utilized to determine a depth of an incision in eye 116. For example, optical system 110 may be utilized to determine a topography of an incision in eye 116.

Optical system 110 may be utilized in a medical procedure. For example, a medical system may include optical system 110. The medical procedure may include an ophthalmic procedure on at least a portion part of eye 116. Although optical system 110 may be utilized in a medical system, optical system 110 may be utilized in any system.

Optical system 110 may include multiple optical devices. For example, an optical device may be or may include a device that controls light (e.g., reflects light, refracts light, filters light, transmits light, polarizes light, etc.). An optical device may be made of any material that controls the light as designed. For example, the material may include one or more of glass, crystal, metal, and semiconductor, among others. Examples of optical devices may include one or more of lenses, mirrors, prisms, optical filters, waveguides, waveplates, beam expanders, beam collimators, beam splitters, gratings, and polarizers, among others.

As shown, optical system 110 may include a laser 120. Laser 120 may generate a laser beam. In one example, laser 120 may be a device that generates a beam of coherent monochromatic light by stimulated emission of photons from excited atoms or molecules. In another example, laser 120 may be a device that generates a laser beam that includes photons associated with multiple frequencies. A laser beam may have any suitable wavelength, e.g., a wavelength in the infrared (IR), in the visible range, or ultraviolet (UV) range, among others. Pulses of the laser beam may have a pulse duration in any suitable range, e.g., the microsecond, nanosecond, picosecond, femtosecond, or attosecond range, among others. The focus of the laser beam may be a focal point of the laser beam. As illustrated, optical system may include detector optics 122 and focusing optics 140. As shown, detector optics 122 may include a polarizer 124, a lens 128, a two-photon absorption (TPA) detector 130, and a waveplate 134. Although lens 128 is shown as a single lens, lens 128 may be multiple lenses.

Polarizer 124 may be an optical filter that transmits light of a specific polarization direction while reflecting light of other polarization directions. Polarizer 124 may filter light of undefined or mixed polarization into light with a single linear polarization. In one example, polarizer 124 may transmit at least a portion of the laser beam received from laser 120 (which may have a first polarization) towards waveplate 134. In another example, polarizer 124 may reflect at least portion of the laser beam received from waveplate 134 (which may have a second polarization) towards lens 128 and TPA detector 130. The first polarization may be a linear polarization. The second polarization may be the linear polarization rotated by ninety degrees (90°). Lens 128 may focus the beam from polarizer 124 to TPA detector 130. For example, TPA detector 130 may be located at a focal plane of lens 128. Lens 128 may be an achromatic lens. For example, lens 128 may be configured to limit effects of one or more chromatic aberrations and/or one or more spherical aberrations, among others.

Waveplate 134 may be an optical device that alters a polarization of light travelling through it. Waveplate 134 may be any suitable waveplate, e.g., a quarter-waveplate, which may convert linearly polarized light into circularly polarized light and vice versa, or a combination of a half-waveplate (which may rotate linearly polarized light by forty-five degrees (45°)) and a forty-five degree (45°) Faraday rotator (also known as an optical diode when used in combination with polarizer 124). Waveplate 134 may be a quarter-waveplate that may receive the laser beam with a first linear polarization from polarizer 124. Waveplate 134 may convert the laser beam from the first linear polarization to a circular polarization. Waveplate 134 may direct the laser beam to focusing optics 140. Waveplate 134 may receive at least a reflected portion of the laser beam from focusing optics 140. Waveplate 134 may convert the at least the reflected portion of the laser beam from focusing optics 140 from a circular polarization to a second linear polarization rotated relative to a first linear polarization. Waveplate 134 may change the original linear polarization of the laser beam by ninety degrees (90°).

Waveplate 134 may include a combination of a half-waveplate and a Faraday rotator. Waveplate 134 may receive the laser beam with a first linear polarization from polarizer 124. In this direction, the half-waveplate and the Faraday rotator may compensate for each other's rotational effect, which may result in a rotation of the laser beam by zero degrees (0°). Waveplate 134 may then direct the laser beam to focusing optics 140. Waveplate 134 may also receive the at least the reflected portion of the laser beam reflected from focusing optics 140. In this direction, the half-waveplate and the Faraday rotator may add rotational effects, which may result in a rotation of the laser beam by ninety degrees (90°), which may be a second linear polarization rotated relative to the first linear polarization. For example, the laser beam may pass through waveplate 134, which may rotate the beam by zero degrees (0°), and may be reflected back through waveplate 134, which may rotate the beam by ninety degrees (90°), resulting in a change from the original linear polarization of the laser beam by ninety degrees (90°). Waveplate 134 may be reconfigured such that the laser beam may pass through waveplate 134, which may rotate the beam by ninety degrees (90°), and may be reflected back through waveplate 134, which may rotate the beam by zero degrees (0°).

Although not specifically illustrated, optical system 110 may not include waveplate 134. For example, polarizer 124 may be replaced with a partially reflecting mirror. Although not specifically illustrated, detector optics 122 may be positioned between beam expander 141 and scanner 144.

As illustrated, focusing optics 140 may include a beam expander 141, a scanner 144, and an objective lens 148. Objective lens 148 may include multiple lenses. In one example, objective lens 148 may be or include a compound lens. In another example, objective lens 148 may be or include a F-theta lens. As shown, beam expander 141 may include lenses 142A and 142B. Although beam expander 141 is shown with two lenses, beam expander 141 may include any number of lenses.

A direction of the laser beam, as the laser beam approaches surface 112, may be parallel to a Z-axis. Surface 112 may be parallel to a X-axis and perpendicular to the Z-axis. Although a Y-axis is not specifically illustrated, the Y-axis may be perpendicular to the X-axis and the Z-axis. For example, the Y-axis may be perpendicular to a plane that includes the X-axis and the Z-axis.

Figure 2A:
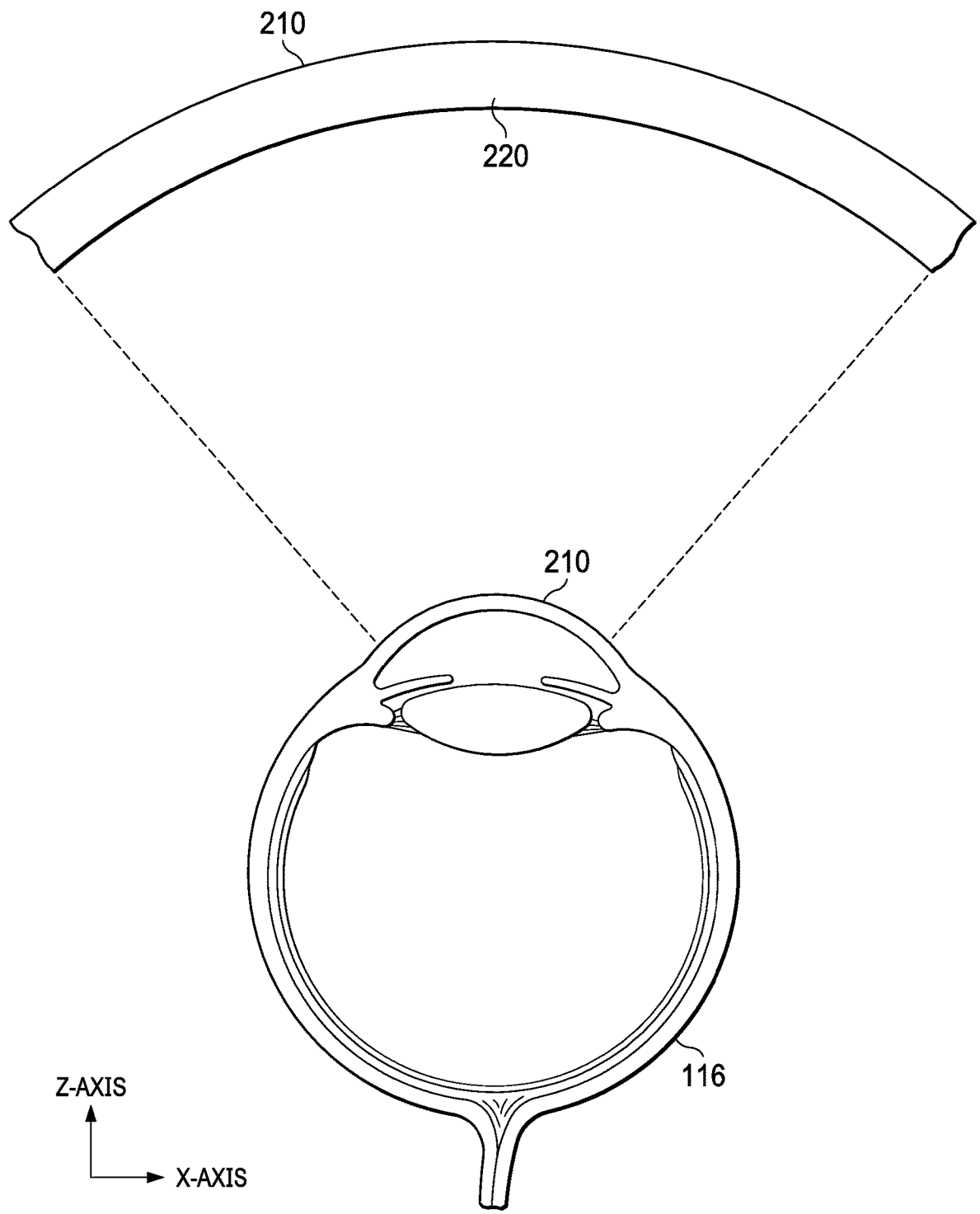
FIG. 2A illustrates a surface of a cornea of an eye.
Figure 2B:
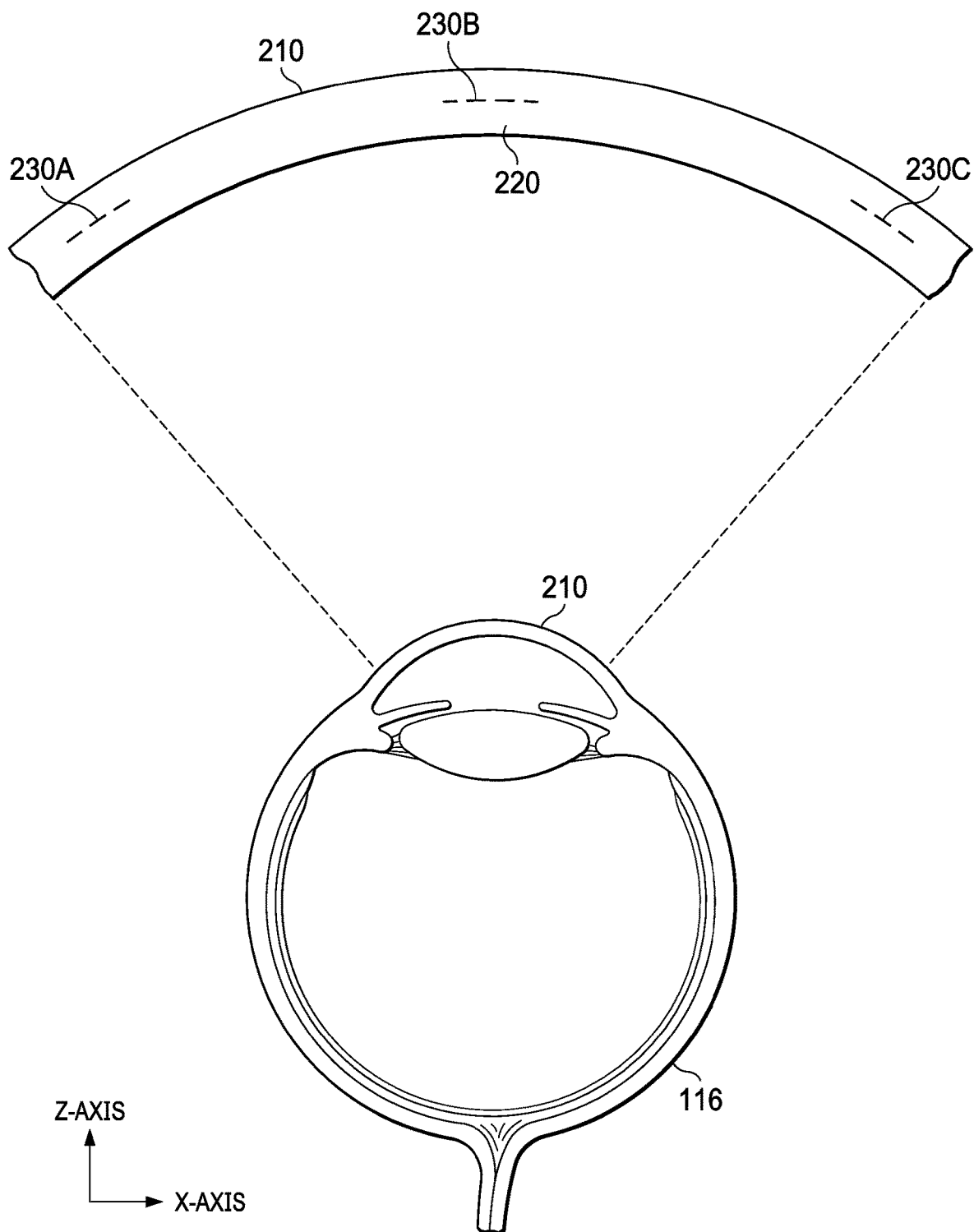
FIG. 2B illustrates incisions in an eye.

Focusing optics 140 may direct and/or may focus the laser beam towards eye 116. In one example, focusing optics 140 may direct and/or may focus the laser beam towards a surface 210 of eye 116, as illustrated in FIG. 2A. Surface 210 may be a surface of a cornea 220 of eye 116. In another example, focusing optics 140 may direct and/or may focus the laser beam towards one or more incisions 230A-230C, as shown in FIG. 2B. Focusing optics 140 may direct a focal point of the laser beam parallel to or along the Z-axis towards eye 116. Focusing optics 140 may receive at least a portion of the beam reflected by surface 210. Focusing optics 140 may receive at least a portion of the beam reflected by an incision 230.

An optical device, such as a lens 142A and/or a mirror, may control a Z-position of a focal point of a laser beam. Another optical device, such as a lens 142B (e.g., in combination with lens 142A), may expand a diameter of a laser beam. In one example, beam expander 141 may be configured to control a focal point of a laser beam. In another example, optics may vary over time such that the Z-position of the focal point changes.

Scanner 144 may include one or more optical devices that may control a direction of a laser beam to control the XY-position of the focal point. To transversely deflect the laser beam, scanner 144 may include a pair of galvanometric actuated scanner mirrors that may tilt about mutually perpendicular axes. Scanner 144 may receive the laser beam from beam expander 141. Scanner 144 may manipulate the laser beam to control the XY-position of the focal point. Objective lens 148 may receive the laser beam from the scanner 144. Objective lens 148 may direct the laser beam to eye 116.

As illustrated in FIG. 1B, a patient interface 114 may stabilize a position of a surface 112 relative to optical system 110. In one example, surface 112 may be a surface of an applanation plane. Although surface 112 is illustrated, surface 112 may not be present. In another example, patient interface 114 may be made of one or more rigid materials (e.g., plastic, glass, metal, etc.). A patient interface 114 may shape an eye (e.g., flatten or otherwise deform) a surface of eye 116. Patient interface may include an applanation plane. A "target-side" surface of patient interface 114 may be the surface of interface 114 designed to face (and may even be in contact with) eye 116. A patient interface 114 may be a one-time-use product. For example, a patient interface 114 may be utilized with an eye of a patient and then discarded. Multiple patient interfaces 114 may be configured with a consistent length in a Z-direction. Multiple patient interfaces 114 may have different respective lengths. A calibration of a Z-position of a point with respect to a particular patient interface 114 may be performed.

As illustrated, optical system 110 may include a computer system 152. Computer system 152 may execute instructions in implementing at least a portion of one or more systems, one or more flow charts, one or more processes, and/or one or more methods described herein. Although optical system 110 is illustrated as including computer system 152, optical system 110 may not include computer system 152. For example, computer system 152 may be external to optical system 110. Computer system 152 may be communicatively coupled to optical system 110.

Focusing optics 140 may direct a laser beam to eye 116. For example, eye 116 may be located at an end of a patient interface 114. Surface 210 of eye 116 may reflect at least a portion of the laser beam. Incision 230 may reflect at least a portion of the laser beam. Detector optics 122 may direct the at least the portion of the laser beam TPA detector 130. For example, TPA detector 130 may transform an intensity of the at least the portion of the laser beam into digital data. The digital data may represent the intensity of the at least the portion of the laser beam. TPA detector 130 may provide the digital data to computer system 152.

The at least the portion of the laser beam may cause two-photon absorption that may excite electrons, which may generate a signal in response to an intensity of incident radiation. The signal may indicate a proximity of a focal point of the laser beam to surface 210 or incision 230. In one example, the farther away the focal point is from surface 210 or incision 230, the lower an intensity of the beam at a portion TPA detector 130. In a second example, the larger a diameter of the at least the portion of the laser beam, the lower an intensity of the beam at a portion TPA detector 130. In a third example, the closer the focal point is to surface 210 or incision 230, the higher an intensity of the beam at a portion TPA detector 130. In a fourth example, the smaller a diameter of the at least the portion of the laser beam, the higher an intensity of the beam at a portion TPA detector 130. In another example, when the focal point is at surface 210 or incision 230, a diameter at TPA detector 130 may be at a minimum, and an intensity may be at a maximum.

As illustrated, computer system 152 may be communicatively coupled to TPA detector 130. As shown, computer system 152 may be communicatively coupled to laser 120. As illustrated, computer system 152 may be communicatively coupled to beam expander 141. As shown, computer system 152 may be communicatively coupled to scanner 144. In one example, computer system 152 may receive information from one or more of laser 120, TPA detector 130, beam expander 141, and scanner 144, among others. In another example, computer system 152 may provide information to one or more of laser 120, TPA detector 130, beam expander 141, and scanner 144, among others. Computer system 152 may provide control information to one or more of laser 120, TPA detector 130, beam expander 141, and scanner 144, among others.

Computer system 152 may determine a focal point of a laser beam in response to intensity measurements from TPA detector 130. Computer system 152 may determine if an intensity is a maximum intensity. The maximum intensity may be the maximum of intensities may be measured at different positions of a focal point. The maximum intensity may be measured or calculated prior during a calibration session. If the intensity is the maximum intensity, computer system 152 may determine that the focal point is at surface 210 or incision 230. If the intensity is not the maximum intensity, computer system 152 may adjust focusing optics 140 to direct a focal point to a different point of the Z-axis. Computer system 152 may generate, from one or more TPA detector signals, a graph that may represent intensities of the at least the portion of the laser beam. For example, the one or more TPA detector signals may be or include data.

An analog to digital converter (ADC) may transform signals from TPA detector 130 associated with the multiple intensities into digital data that represents multiple measurements of the multiple intensities. For example, computer system 152 may utilize the digital data that represents multiple measurements of the multiple intensities. Computer system 152 may include the ADC. The ADC may be external to computer system 152. TPA detector 130 may include the ADC. For example, TPA detector 130 may provide digital data that represents multiple measurements of the multiple intensities.

Figure 3A:
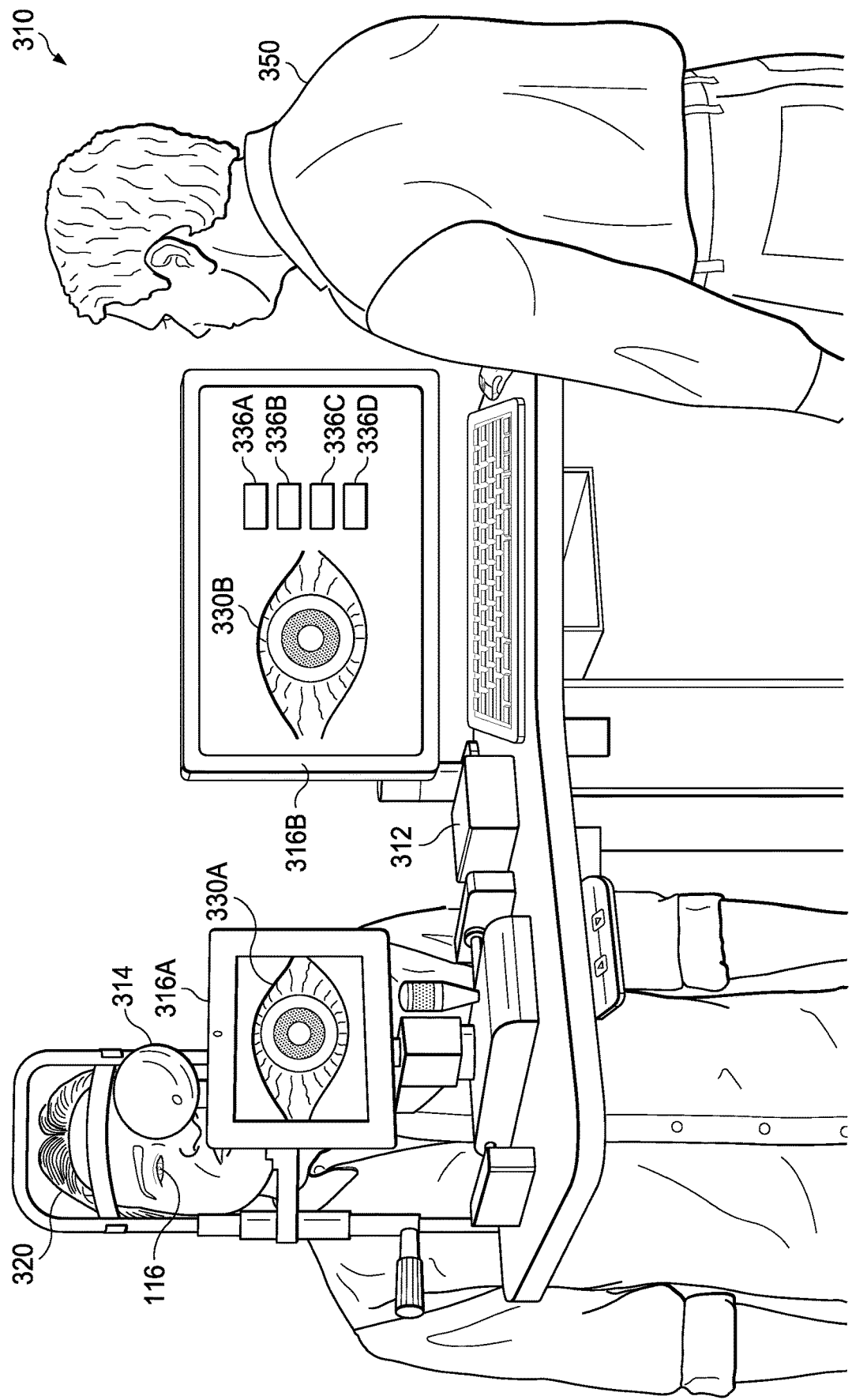
FIG. 3A illustrates an example of a medical system.

Turning now to FIG. 3A, an example of a medical system is illustrated. As shown, a medical system 310 may be utilized with a patient 320. As illustrated, medical system 310 may include a computer system 312. Computer system 312 may be communicatively coupled to displays 316A and 316B. Computer system 312 may be communicatively coupled to a biometry device 314. In one example, biometry device 314 may include one or more cameras. In another example, biometry device 314 may include a three-dimensional scanner. Biometry device 314 may be utilized in biometry of an eye 116 of patient 320. As shown, display 316A may display an image 330A associated with eye 116 of patient 320. As illustrated, display 316B may display an image 330B associated with eye 116 of patient 320.

Computer system 312 may determine eye recognition information. For example, the eye recognition information may include biometry information associated with eye 116 of patient 320. The biometry information associated with eye 116 may include one or more of a pattern of blood vessels of a sclera of eye 116, a structure of an iris of eye 116, a position of a structure of an iris of eye 116, a distance measurement of a cornea of eye 116 to a lens of eye 116, a distance measurement of a lens of eye 116 to a retina of eye 116, a corneal topography of eye 116, a retinal pattern of eye 116, and a wavefront measurement, among others.

As shown, display 316B may display display areas 336A-336D. In one example, a display area 336 may display a distance measurement of a cornea of eye 116 to a lens of eye 116, a distance measurement of a lens of eye 116 to a retina of eye 116, a position of a structure of an iris 334, corneal topography information, or wavefront measurement information, among other biometry information associated with eye 116. In another example, a display area 336 may display any information associated with patient 320.

A person 350 may operate medical system 310. For example, person 350 may be medical personnel. Person 350 may enter identification information associated with patient 320 into computer system 312. The identification information associated with patient 320 may include one or more of a name of patient 320, an address of patient 320, a telephone number of patient 320, a government issued identification number of patient 320, a government issued identification string of patient 320, and a date of birth of patient 320, among others.

Person 350 may provide medical procedure information, associated with patient 320, to computer system 312. The medical procedure information may be associated with a medical procedure. The medical procedure information may be associated identification information associate with patient 320. Computer system 312 may store the medical procedure information. For example, computer system 312 may store the medical procedure information for later utilization. The medical procedure information may be associated with a surgery. For example, the medical procedure information may be retrieved before the surgery. The medical procedure information may be utilized during a medical procedure. For example, the medical procedure may include a surgery.

Figure 3B:
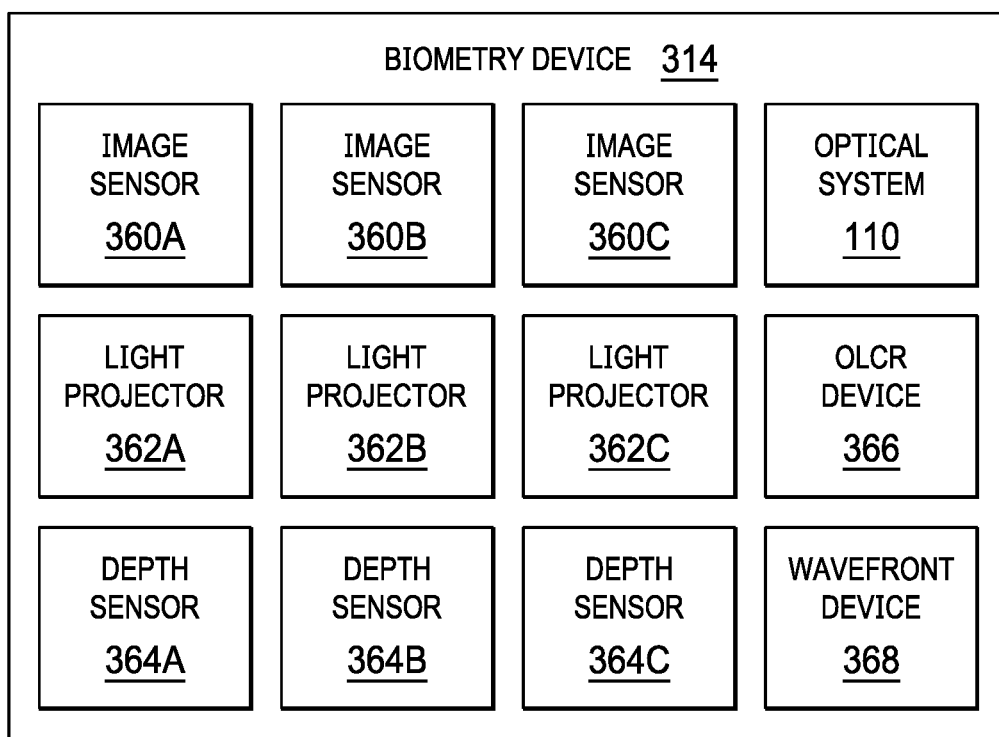
FIG. 3B illustrates an example of a biometry device.

Turning now to FIG. 3B, an example of a biometry device is illustrated. As shown, biometry device 314 may include image sensors 360A-360C. For example, an image sensor 360 may include a camera. A camera may include a one or more digital image sensors. In one example, a digital image sensor may include a charge-coupled device (CCD). In another example, a digital image sensor may include a complementary metal-oxide-semiconductor (CMOS). The camera may transform light into digital data. The camera may utilize a Bayer filter mosaic. For example, the camera may utilize a Bayer filter mosaic in combination with an optical anti-aliasing filter. A combination of the Bayer filter mosaic in combination with the optical anti-aliasing filter may reduce aliasing due to reduced sampling of different primary-color images. The camera may utilize a demosaicing process. For example, the demosaicing process may be utilized to interpolate color information to create a full array of red, green, and blue (RGB) image data.

As illustrated, biometry device 314 may include light projectors 362A-362C. In one example, a light projector 362 may project visible light. In another example, a light projector 362 may project infrared light. A light projector 362 may project circles and/or dots onto an eye of a patient. An image sensor 360 may receive reflections of the circles and/or the dots that were projected onto the eye of the patient. A computer system may determine one or more locations and/or one or more templates associated with the eye of the patient based at least on the reflections of the circles and/or the dots that were projected onto the eye of the patient. As shown, biometry device 314 may include depth sensors 364A-364C. A depth sensor 364 may include a light projector 362. A depth sensor 364 may include an optical sensor. As illustrated, biometry device 314 may include an optical low coherence reflectometer (OLCR) device 366. As shown, biometry device 314 may include a wavefront device 368.

Wavefront device 368 may include one or more of a light source and a wavefront sensor, among others. A light source may provide a first light wave to eye 116. A wavefront sensor may receive a first perturbed light wave, based at least on the first light wave, from eye 116. In one example, wavefront device 368 may determine first optical corrections based at least on the first perturbed light. In another example, a computer system may determine first optical corrections based at least on the first perturbed light. Wavefront device 368 may provide data, based at least on the first perturbed light wave, to a computer system. For example, the computer system may determine first optical corrections based at least on the data from wavefront device 368.

Any two or more of an image sensor 360, a light projector 362, a depth sensor 364, an OLCR device 366, and a wavefront device 368 may be combined. One or more of image sensors 360A-360C, one or more of light projectors 362A-362C, one or more of depth sensors 364A-364C, OLCR device 366, and/or wavefront device 368, among others, may produce data that may be utilized by a computer system. As illustrated, biometry device 314 may include an optical system 110.

Figure 4A:
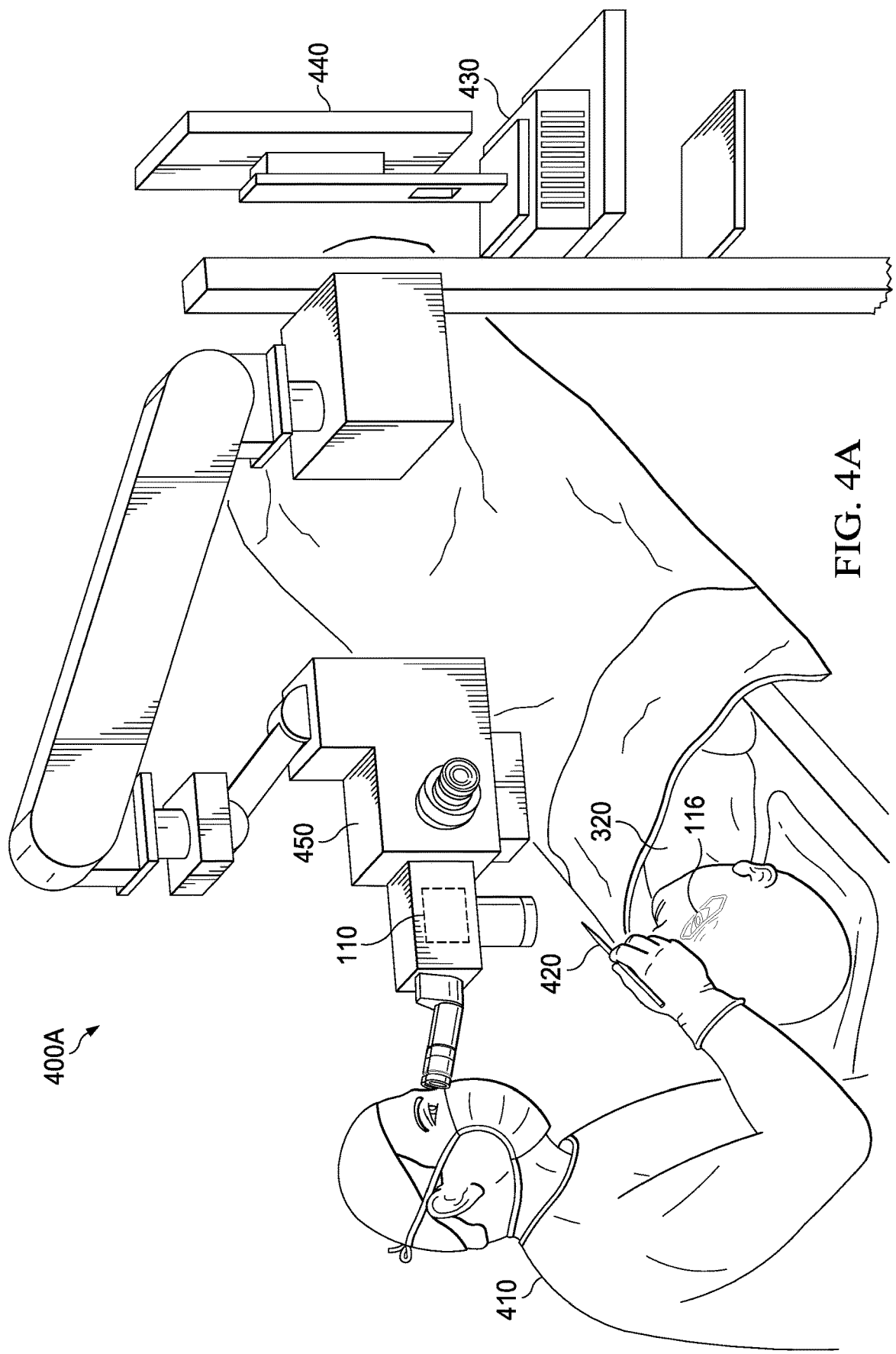
FIG. 4A illustrates a second example of a medical system.

Turning now to FIG. 4A, a second example of a medical system is illustrated. As shown, a surgeon 410 may utilize surgical tooling equipment 420. In one example, surgeon 410 may utilize surgical tooling equipment 420 in a surgery involving eye 116 of patient 320. A medical system 400A may include an ophthalmic surgical tool tracking system. As illustrated, medical system 400A may include a computer system 430, a display 440, and a microscope integrated display (MID) 450.

Computer system 430 may receive image frames captured by one or more image sensors. For example, computer system 430 may perform various image processing on the one or more image frames. Computer system 430 may perform image analysis on the one or more image frames to identify and/or extract one or more images of surgical tooling equipment 420 from the one or more image frames. Computer system 430 may generate a graphical user interface (GUI), which may overlay the one or more image frames. For example, the GUI may include one or more indicators and/or one or more icons, among others. The one or more indicators may include surgical data, such as one or more positions and/or one or more orientations. The one or more indicators may include one or more warnings. The GUI may be displayed by display 440 and/or MID 450 to surgeon 410 and/or other medical personnel.

Computer system 430, display 440, and MID 450 may be implemented in separate housings communicatively coupled to one another or within a common console or housing. A user interface may be associated with one or more of computer system 430, display 440, and MID 450, among others. For example, a user interface may include one or more of a keyboard, a mouse, a joystick, a touchscreen, an eye tracking device, a speech recognition device, a gesture control module, dials, and/or buttons, among other input devices. A user (e.g., surgeon 410 and/or other medical personnel) may enter desired instructions and/or parameters via the user interface. For example, the user interface may be utilized in controlling one or more of computer system 430, display 440, and MID 450, among others. As illustrated, MID 450 may include an optical system 110.

Figure 4B:
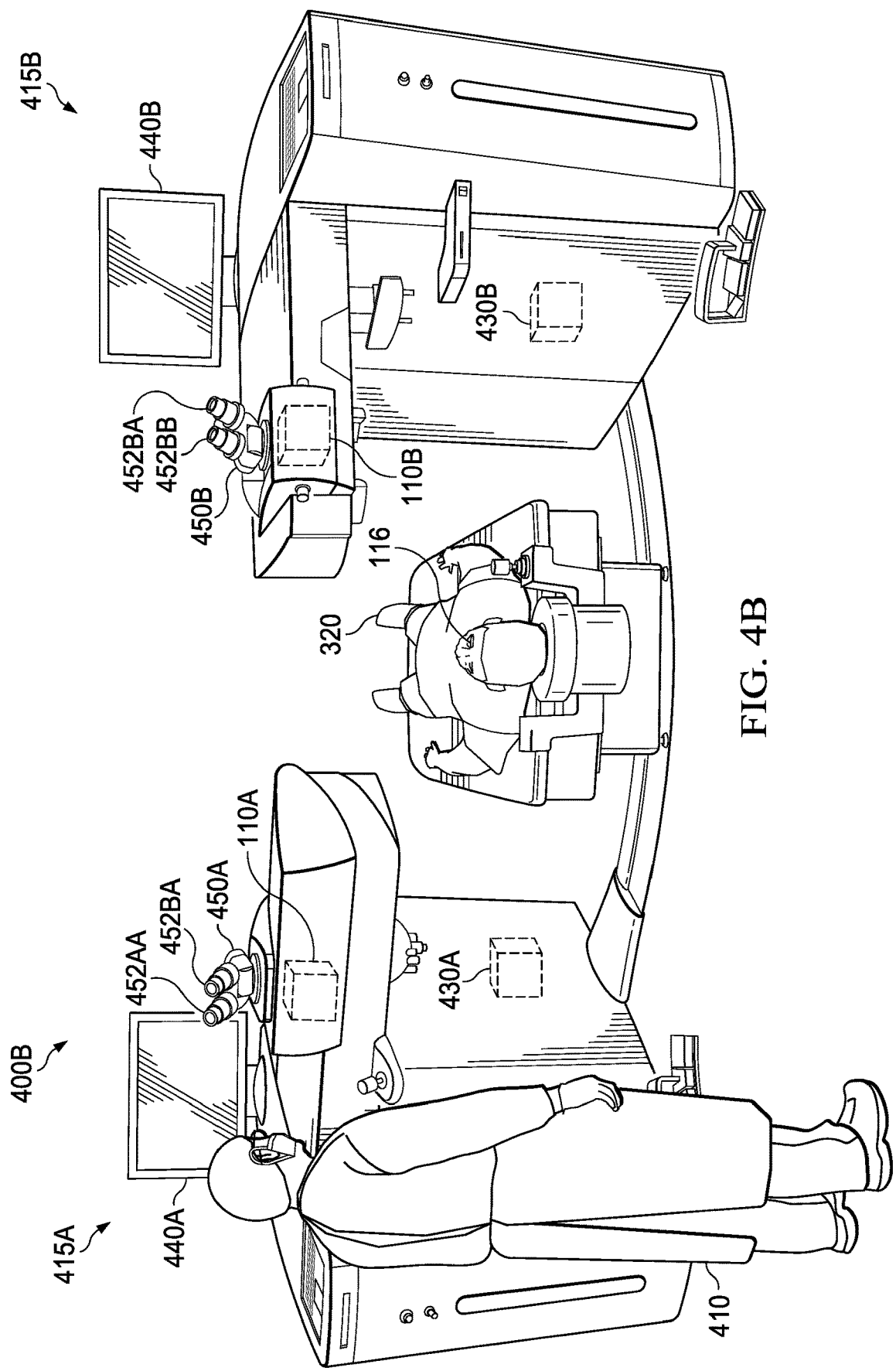
FIG. 4B illustrates a third example of a medical system.

Turning now to FIG. 4B, a third example of a medical system is illustrated. As shown, a surgeon 410 may utilize a system 400B. For example, surgeon 410 may utilize system 400B in a surgery involving eye 116 of patient 320. System 400B may include multiple systems. As shown, system 400B may include a cutting system 415A. For example, surgeon 410 may utilize system 415A in cutting eye 116. Eye 116 may include a flap in a cornea of an eye of patient 320. As illustrated, system 400B may include a shaping system 415B. For example, surgeon 410 may utilize shaping system 415B in performing ablation on an interior part of the cornea of eye 116.

As shown, system 415A may include a display 440A. As illustrated, system 415A may include a MID 450A. As illustrated, MID 450A may include eye pieces 452AA and 452AB. An eye piece 452A may refer to an eye piece 452AA or to an eye piece 452BA. An eye piece 452B may refer to an eye piece 452AB or to an eye piece 452BB. System 415A may include one or more of image sensors 360A-360C, one or more of light projectors 362A-362C, one or more of depth sensors 364A-364C, OLCR device 366, wavefront device 368, and/or an optical system 110A, among others. As illustrated, system 415B may include a display 440B. As shown, system 415B may include a MID 450B. As illustrated, MID 450B may include eye pieces 452BA and 452BB. System 415B may include one or more of image sensors 360A-360C, one or more of light projectors 362A-362C, one or more of depth sensors 364A-364C, OLCR device 366, and/or wavefront device 368, among others. As shown, system 415B may include an optical system 110B.

System 415A may include a laser, such as a femtosecond laser, which may use short laser pulses to separate a series of small portions of corneal tissue to form a flap that may be lifted up to expose an interior part of the cornea. The flap may be planned and cut using one or both of cutting device displays 440A and 450A, along with control devices and a computer system 430A. As shown, system 415A may include computer system 430A. For example, computer system 430A may be communicatively coupled to one or more of image sensors 360A-360C, one or more of light projectors 362A-362C, one or more of depth sensors 364A-364C, OLCR device 366, wavefront device 368, and/or optical system 110A, among others, of system 415A. As illustrated, system 415B may include computer system 430B. For example, computer system 430B may be communicatively coupled to one or more of image sensors 360A-360C, one or more of light projectors 362A-362C, one or more of depth sensors 364A-364C, OLCR device 366, wavefront device 368, and/or optical system 110B among others, of system 415B.

Systems 415A and 415B may be physically separated as shown in FIG. 4B. Patient 320 may be moved between systems 415A and 415B. Alternatively, patient 320 may remain stationary and systems 415A and 415B may be moved to patient 320. Systems 415A and 415B may be physically combined into a single unitary device, such that neither the device nor patient 320 is repositioned when switching between systems 415A and 415B.

System 400B may include one or more control devices for controlling systems 415A and 415B. For example, the one or more control devices may include one or more of an interactive display, such as a touchscreen display, a keyboard, a mouse, a touchpad, buttons, a joystick, a foot pedal, a heads-up display, and virtual-reality glasses, or other devices able to interact with a user, such as medical personnel.

System 400B may include at least one computer system configured to generate an image presented on at least one of displays 440A, 450A, 440B, and 450B, among others. For example, the at least one computer system may include one or more of computer systems 430A and 430B. One or more of computer systems 430A and 430B may be communicatively coupled to observational devices, such as a microscope, a camera, an optical coherence tomography (OCT) device or display, or another device able to measure the position of the eye undergoing surgery. One or more of computer systems 430A and 430B may be communicatively coupled to one or more of the control devices.

In one example, cutting device computer system 430A: i) may be communicatively coupled to observational devices that observe the eye when patient 320 is positioned with system 415A, ii) may provide graphical information regarding the planned flap location and the planned area of ablation to one or more of displays 440A and 450A, and iii) may be communicatively coupled to one or more control devices of system 415A. In a second example, shaping device computer 430B: i) may be communicatively coupled to observational devices that observe the eye when patient 320 is positioned with a shaping device, ii) may provide graphical information regarding the planned flap location and the planned area of ablation to one or more of displays 440B and 450B, and iii) may be communicatively coupled to one or more control devices of system 415B. In another example, a computer system may include the properties and/or the attributes described above with respect to one or more of computer systems 430A and 430B, among others.

A computer system of a system 400 may be communicatively coupled to another part of system 400 in a wired fashion or in a wireless fashion. One of more of computer systems of system 400 may be communicatively coupled to a database, stored locally, on a remote computer system or a remote data center, or both, that store patient data, treatments plans, and/or other information associated with medical treatments and/or system 400. In one example, the database may include a relational database. In a second example, the database may include a graph database. In another example, the database may include a "Not Only SQL" (NoSQL) database.

System 400 may enter information regarding patient 320 and the treatment to be performed on patient 320 or actually performed on patient 320. System 400 may allow a user to enter and view information regarding patient 320 and the treatment to be performed on patient 320. Such data may include information about patient 320, such as identifying information, a medical history of patient 320, and/or information about eye 116 being treated, among others. Such data may include information about the treatment plans, such as the shape and location of a corneal cut and/or a shape and location of ablation, among others.

Figure 4C:
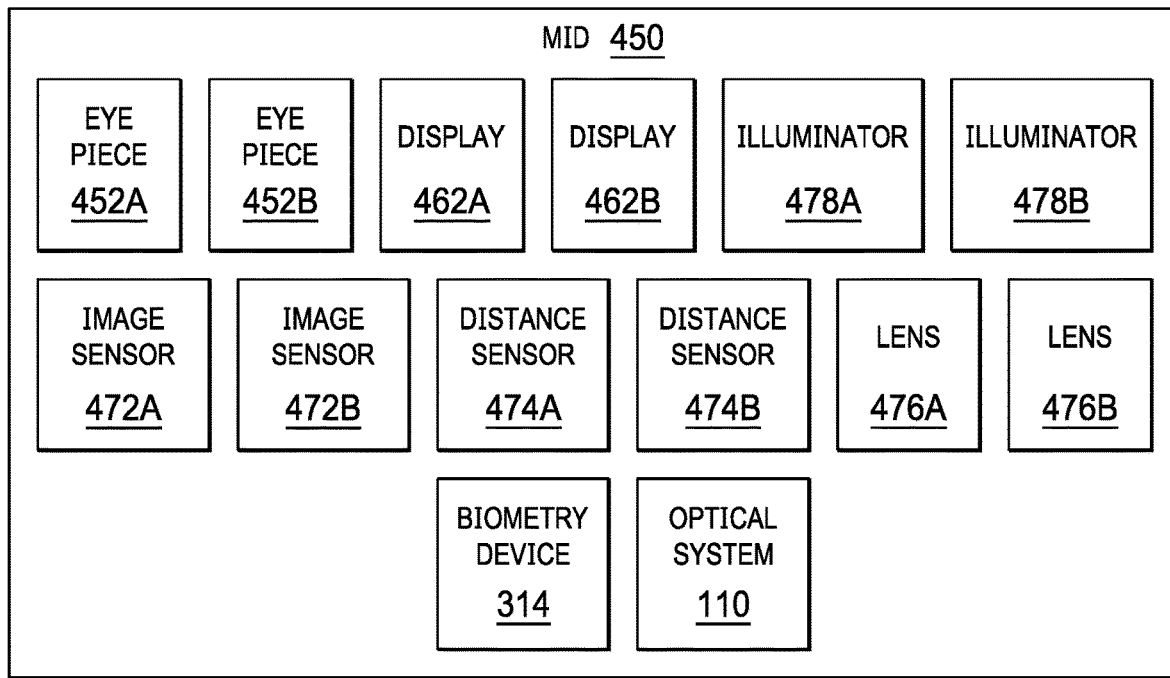
FIG. 4C illustrates an example of a microscope integrated display and examples of surgical tooling equipment.
Figure 4C:
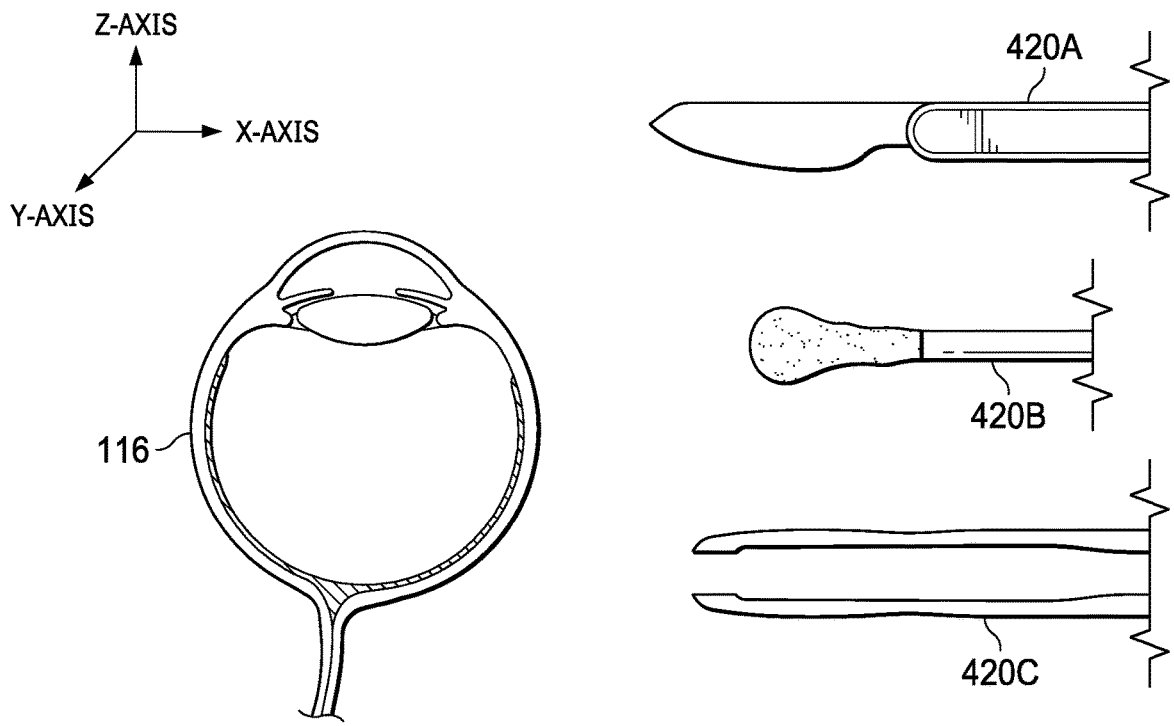

Turning now to FIG. 4C, an example of a microscope integrated display and examples of surgical tooling equipment are illustrated. As shown, surgical tooling equipment 420A may be or include a scalpel. As illustrated, surgical tooling equipment 420B may be or include a Q-tip. As shown, surgical tooling equipment 420C may be or include tweezers. Other surgical tooling equipment that is not specifically illustrated may be utilized with one or more systems, one or more processes, and/or one or more methods described herein.

As an example, surgical tooling equipment 420 may be marked with one or more patterns. The one or more patterns may be utilized in identifying surgical tooling equipment 420. The one or more patterns may include one or more of a hash pattern, a stripe pattern, and a fractal pattern, among others. As another example, surgical tooling equipment 420 may be marked with a dye and/or a paint. The dye and/or the paint may reflect one or more of visible light, infrared light, and ultraviolet light, among others. In one example, an illuminator 478 may provide ultraviolet light, and image sensor 472 may receive the ultraviolet light reflected from surgical tooling equipment 420. Computer system 430 may receive image data, based at least on the ultraviolet light reflected from surgical tooling equipment 420, from image sensor 472 and may utilize the image data, based at least on the ultraviolet light reflected from surgical tooling equipment 420, to identify surgical tooling equipment 420 from other image data provided by image sensor 472. In another example, an illuminator 478 may provide infrared light, and image sensor 472 may receive the infrared light reflected from surgical tooling equipment 420. Computer system 430 may receive image data, based at least on the infrared light reflected from surgical tooling equipment 420, from image sensor 472 and may utilize the image data, based at least on the infrared light reflected from surgical tooling equipment 420, to identify surgical tooling equipment 420 from other image data provided by image sensor 472.

As illustrated, MID 450 may include eye pieces 452A and 452B. As shown, MID 450 may include displays 462A and 462B. Surgeon 410 may look into eye pieces 452A and 452B. In one example, display 462A may display one or more images via eye piece 452A. A left eye of surgeon 410 may utilize eye piece 452A. In another example, display 462B may display one or more images via eye piece 452B. A right eye of surgeon 410 may utilize eye piece 452B. Although MID 450 is shown with multiple displays, MID 450 may include a single display 462. For example, the single display 462 may display one or more images via one or more of eye pieces 452A and 452B. MID 450 may be implemented with one or more displays 462.

As shown, MID 450 may include image sensors 472A and 472B. In one example, image sensors 472A and 472B may acquire images. In a second example, image sensors 472A and 472B may include cameras. In another example, an image sensor 472 may acquire images via one or more of visible light, infrared light, and ultraviolet light, among others. One or more image sensors 472A and 472B may provide data of images to computer system 430. Although MID 450 is shown with multiple image sensors, MID 450 may include a single image sensor 472. MID 450 may be implemented with one or more image sensors 472.

As illustrated, MID 450 may include distance sensors 474A and 474. For example, a distance sensor 474 may determine a distance to surgical tooling equipment 420. Distance sensor 474 may determine a distance associated with a Z-axis. Although MID 450 is shown with multiple image sensors, MID 450 may include a single distance sensor 474. In one example, MID 450 may be implemented with one or more distance sensors 474. In another example, MID 450 may be implemented with no distance sensor.

As shown, MID 450 may include lenses 476A and 476B. Although MID 450 is shown with multiple lenses 476A and 476B, MID 450 may include a single lens 476. MID 450 may be implemented with one or more lenses 476. As illustrated, MID 450 may include illuminators 478A and 478B. For example, an illuminator 478 may provide and/or produce one or more of visible light, infrared light, and ultraviolet light, among others. Although MID 450 is shown with multiple illuminators, MID 450 may include a single illuminator 478. MID 450 may be implemented with one or more illuminators 478. MID 450 may include one or more structures and/or one or more functionalities as those described with reference to biometry device 314. In one example, MID 450 may include OLCR device 366. In another example, MID 450 may include wavefront device 368. MID 450 may include a biometry device 314. MID 450 may include an optical system 110.

Figure 4D:
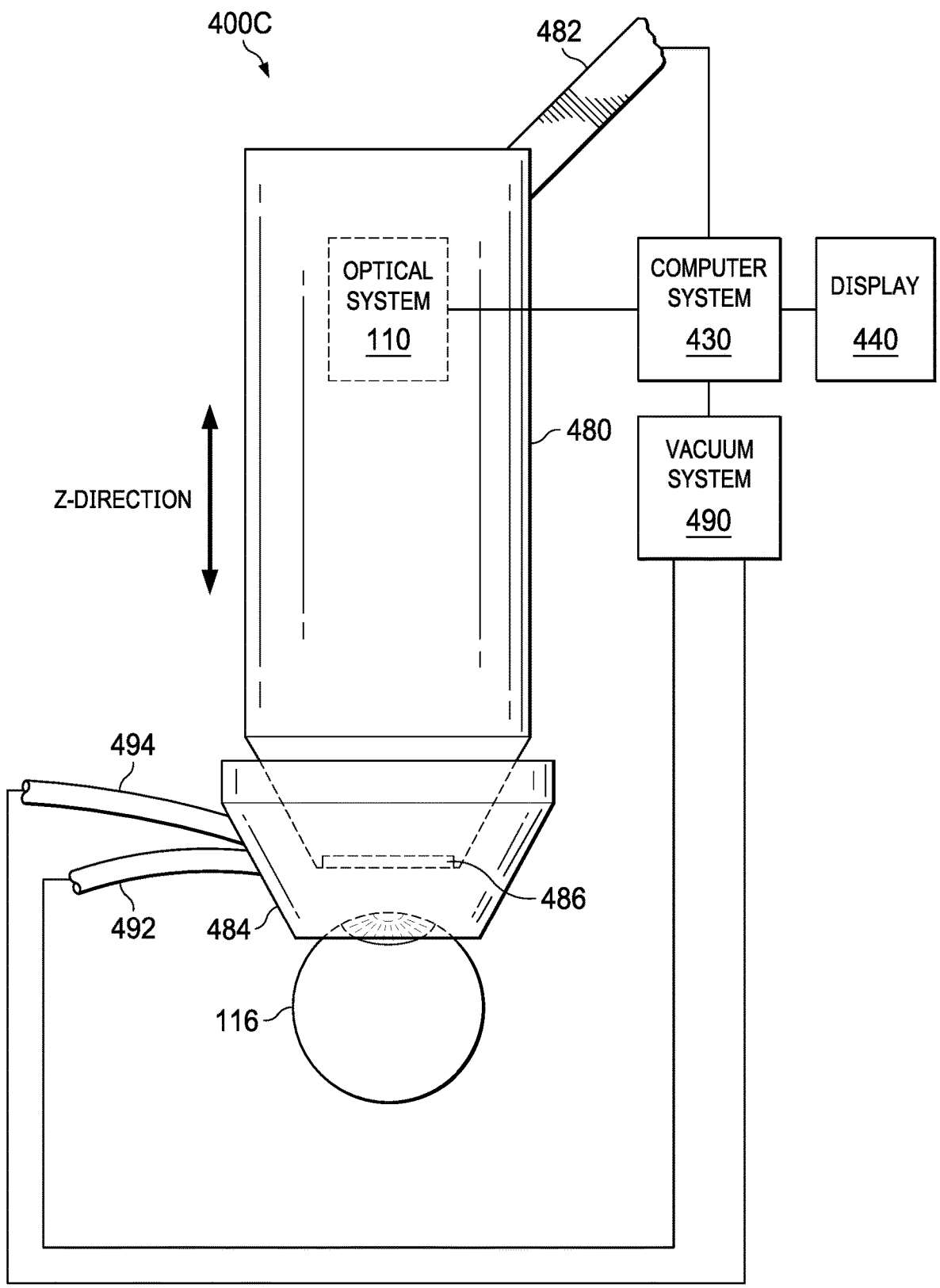
FIG. 4D illustrates another example of a medical system.

Turning now to FIG. 4D, another example of a medical system is illustrated. As shown, a medical system 400C may include a suction cone 480. For example, suction cone 480 may be or include an applanation cone. As illustrated, suction cone 480 may include an optical system 110. As shown, a computer system 430 may be coupled to a control device 482 of suction cone 480. For example, computer system 430 may control suction cone 480 via control device 482. After a suction ring 484 is docked with an eye 116, suction cone 480 may be docked with suction ring 484. As illustrated, suction cone 480 may include a lens 486. Although lens 486 is illustrated as flat or planar, lens 486 may include concave shape and/or may include convex shape. If lens 486 is planar, lens 486 may be referred to as an applanation plane. For example, the applanation plane may include surface 112.

As illustrated, medical system 400C may include a vacuum system 490. As shown, vacuum system 490 may be communicatively coupled to computer system 430. For example, computer system 430 may control vacuum system 490. Vacuum system 490 may create one or more low pressures via one or more of lines 492 and 494. For example, vacuum system 490 may create one or more low pressures via line 494 to adhere and/or seal a suction ring 484 to an eye 116 of a patient. As shown, medical system 400C may include lines 492 and 494 and suction ring 484.

Figure 5:
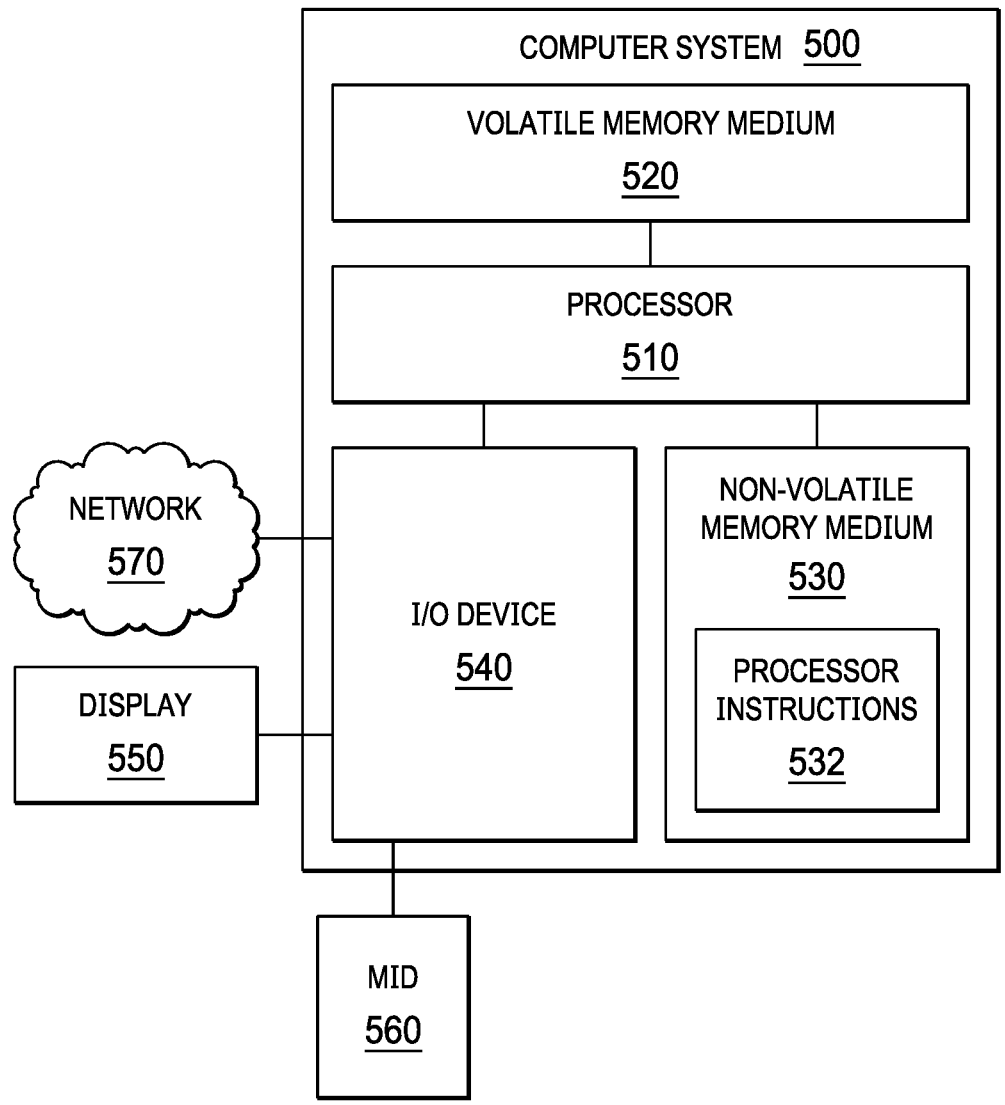
FIG. 5 illustrates an example of a computer system.

Turning now to FIG. 5, an example of a computer system is illustrated. As shown, a computer system 500 may include a processor 510, a volatile memory medium 520, a non-volatile memory medium 530, and an input/output (I/O) device 540. As illustrated, volatile memory medium 520, non-volatile memory medium 530, and I/O device 540 may be communicatively coupled to processor 510.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, and/or one or more combinations of the foregoing. As shown, non-volatile memory medium 530 may include processor instructions 532. Processor instructions 532 may be executed by processor 510. In one example, one or more portions of processor instructions 532 may be executed via non-volatile memory medium 530. In another example, one or more portions of processor instructions 532 may be executed via volatile memory medium 520. One or more portions of processor instructions 532 may be transferred to volatile memory medium 520.

Processor 510 may execute processor instructions 532 in implementing at least a portion of one or more systems, one or more flow charts, one or more processes, and/or one or more methods described herein. For example, processor instructions 532 may be configured, coded, and/or encoded with instructions in accordance with at least a portion of one or more systems, one or more flowcharts, one or more methods, and/or one or more processes described herein. Although processor 510 is illustrated as a single processor, processor 510 may be or include multiple processors. In one example, the multiple processors may execute instructions of a single instruction set architecture (ISA). In another example, at least two of the multiple processors may execute instructions of different instruction set architectures (ISAs). As an example, at least one of the multiple processors may be or include a graphics processor unit (GPU). One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 510 may include any suitable system, device, or apparatus operable to interpret and execute program instructions, process data, or both stored in a memory medium and/or received via a network. Processor 510 may further include one or more microprocessors, microcontrollers, digital signal processors (DSPs), graphics processor units (GPUs), application specific integrated circuits (ASICs), or other circuitry configured to interpret and execute program instructions, process data, or both.

I/O device 540 may include any instrumentality or instrumentalities, which allow, permit, and/or enable a user to interact with computer system 500 and its associated components by facilitating input from a user and output to a user. Facilitating input from a user may allow the user to manipulate and/or control computer system 500, and facilitating output to a user may allow computer system 500 to indicate effects of the user's manipulation and/or control. For example, I/O device 540 may allow a user to input data, instructions, or both into computer system 500, and otherwise manipulate and/or control computer system 500 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 540 may include one or more busses, one or more serial devices, and/or one or more network interfaces, among others, that may facilitate and/or permit processor 510 to implement at least a portions of one or more systems, processes, and/or methods described herein. In one example, I/O device 540 may include a storage interface that may facilitate and/or permit processor 510 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 540 may include a network interface that may facilitate and/or permit processor 510 to communicate with a network. I/O device 540 may include one or more of a wireless network interface and a wired network interface. In a third example, I/O device 540 may include one or more of a peripheral component interconnect (PCI) interface, a PCI Express (PCIe) interface, a serial peripheral interconnect (SPI) interface, and an inter-integrated circuit (I²C) interface, among others. In a fourth example, I/O device 540 may include circuitry that may permit processor 510 to communicate data with one or more sensors. In a fifth example, I/O device 540 may facilitate and/or permit processor 510 to communicate data with one or more of a display 550 and a MID 560, among others. In another example, I/O device 540 may facilitate and/or permit processor 510 to communicate data with an imaging device 570. As illustrated, I/O device 540 may be coupled to a network 580. For example, I/O device 540 may include a network interface.

Network 580 may include a wired network, a wireless network, an optical network, or a combination of the foregoing, among others. Network 580 may include and/or be coupled to various types of communications networks. For example, network 580 may include and/or be coupled to a local area network (LAN), a wide area network (WAN), an Internet, a public switched telephone network (PSTN), a cellular telephone network, a satellite telephone network, or a combination of the foregoing, among others. A WAN may include a private WAN, a corporate WAN, a public WAN, or a combination of the foregoing, among others.

A computer system described herein may include one or more structures and/or one or more functionalities as those described with reference to computer system 500. In one example, computer system 152 may include one or more structures and/or one or more functionalities as those described with reference to computer system 500. In a second example, computer system 312 may include one or more structures and/or one or more functionalities as those described with reference to computer system 500. In a third example, computer system 430 may include one or more structures and/or one or more functionalities as those described with reference to computer system 500. In another example, a computer system of MID 450 may include one or more structures and/or one or more functionalities as those described with reference to computer system 500. Although not specifically illustrated, any device and/or any system may be coupled to a processor of a computer system. For example, any device and/or any system may be communicatively coupled to a processor of a computer system.

Figure 6:
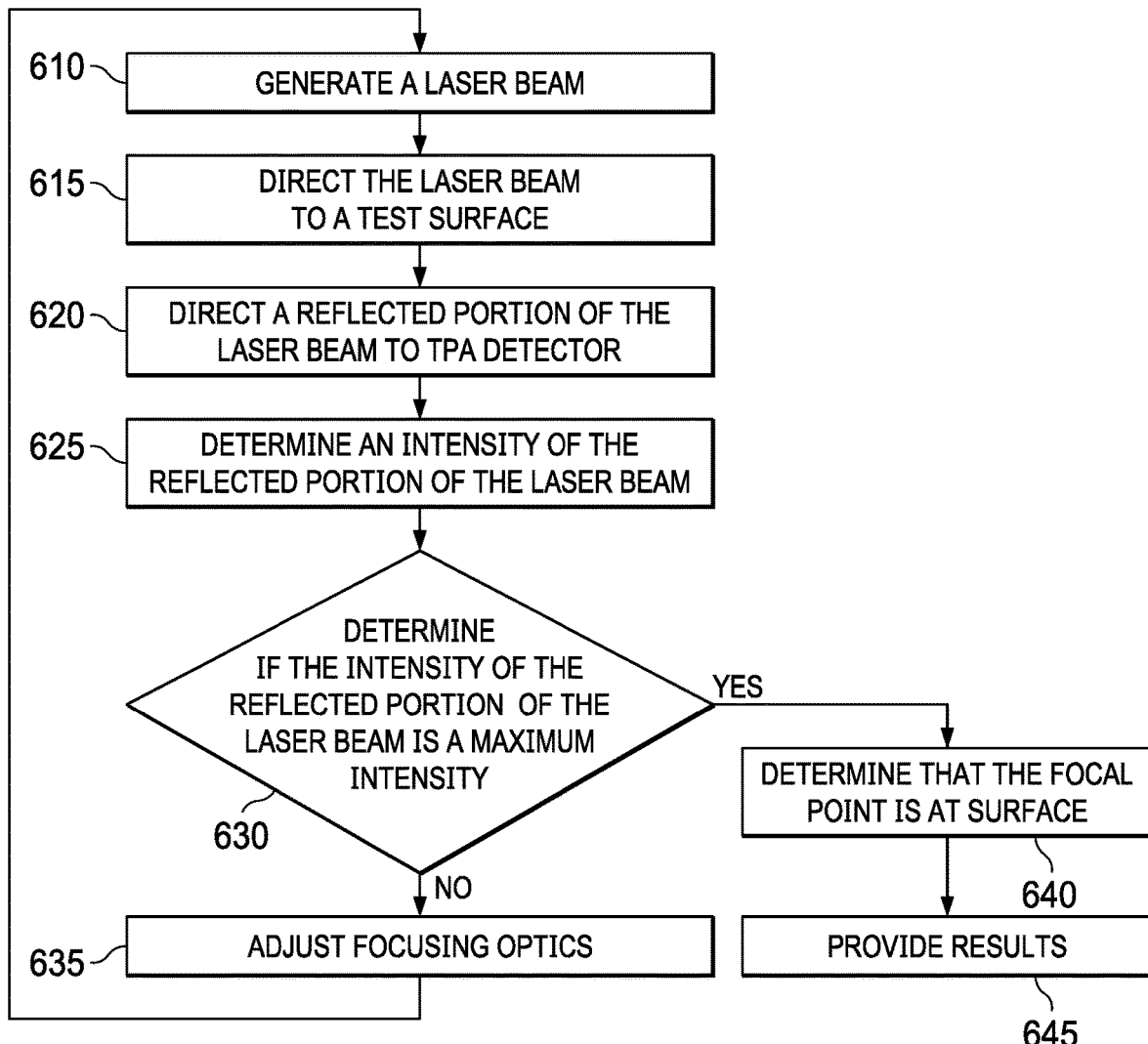
FIG. 6 illustrates an example of a method of operating an optical system.

Turning now to FIG. 6, an example of a method of operating an optical system is illustrated. At 610, a laser beam may be generated. For example, laser 120 may generate a laser beam. Computer system 152 may provide control information, that indicates generating a laser beam, to laser 120. For example, laser 120 may receive the control information from computer system 152 and generate the laser beam in accordance with the control information.

At 615, the laser beam may be directed to a test surface. For example, focusing optics 140 may direct the laser beam to surface 112. Focusing optics 140 may reflect a portion of the laser beam. A remainder of the laser beam may travel to surface 112. At 620, a reflected portion of the laser beam may be directed to TPA detector 130. For example, detector optics 122 may direct the reflected portion of the laser beam to TPA detector 130. The reflected portion of the laser beam may be reflected from surface 112.

At 625, an intensity of the reflected portion of the laser beam may be determined. For example, TPA detector 130 may determine an intensity of the reflected portion of the laser beam. TPA detector 130 may transform the intensity of the reflected portion of the laser beam into digital data that indicates the intensity of the reflected portion of the laser beam. TPA detector 130 may provide the digital data that indicates the intensity of the reflected portion of the laser beam to computer system 152. Computer system 152 may receive the digital data that indicates the intensity of the reflected portion of the laser beam.

At 630, it may be determined if the intensity of the reflected portion of the laser beam is a maximum intensity. For example, computer system 152 may determine, from the digital data that indicates the intensity of the reflected portion of the laser beam, if the intensity of the reflected portion of the laser beam is a maximum intensity. Determining if the intensity of the reflected portion of the laser beam is a maximum intensity may include comparing the intensity of the reflected portion of the laser beam with other one or more intensities of repetitive other reflected portions of the laser beam. For example, computer system 152 may store and/or access the other one or more intensities via memory medium.

If the signal is not at the maximum intensity, focusing optics 140 may be adjusted, at 635. For example, computer system 152 may adjust focusing optics 140. Computer system 152 may provide, to focusing optics 140, control information that indicates at least one adjustment of focusing optics 140. For example, computer system 152 may provide, to beam expander 141, control information that indicates at least one adjustment of one or more of lenses 142A and 142B. Adjusting focusing optics 140 may direct a focal point of the laser beam to a different location with respect to the Z-axis. For example, adjusting focusing optics 140 may direct a focal point of the laser beam toward or away from surface 112. The method may proceed to 610.

If the signal is at the maximum, it may be determined that the focal point is at surface 112, at 640. For example, computer system 152 may determine that the focal point is at surface 112. Interpolation may be utilized to refine a position of surface 112. At 645, results may be provided. For example, computer system 152 may provide results. Providing the results may include one or more of displaying the results via a display, printing the results via a printer, storing the results to a memory medium, and sending the result to a communication network, among others.

Figure 7A:
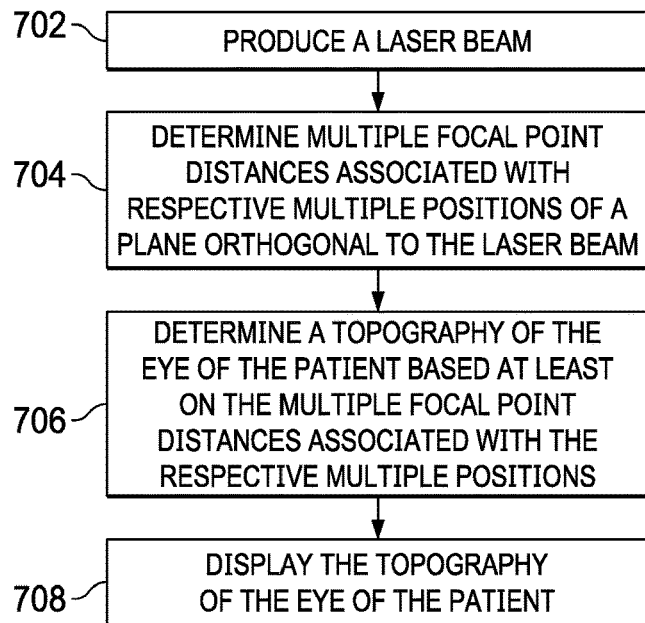
FIG. 7A illustrates an example of a method of determining a topography of an eye of a patient.

Turning now to FIG. 7A, an example of a method of determining a topography of an eye of a patient is illustrated. At 702, a laser beam may be produced. For example, laser 120 may produce a laser beam. Producing a laser beam may include pulsing the laser beam. Pulsing the laser beam may include pulsing the laser beam at femtosecond pulse durations. The laser beam may include photons associated with multiple frequencies.

Figure 9A:
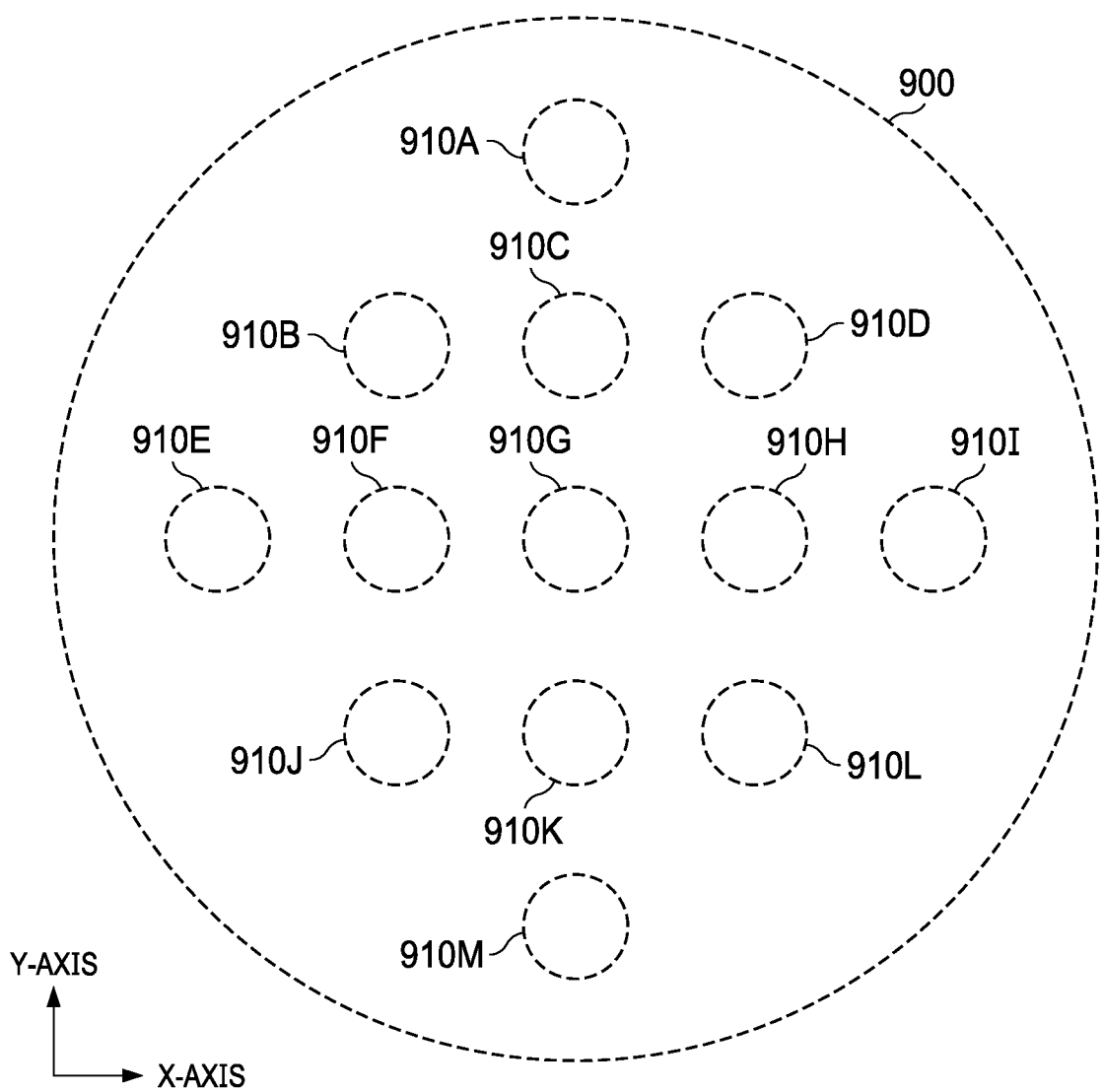
FIG. 9A illustrates an example of a plane and multiple positions of the plane.
Figure 9B:
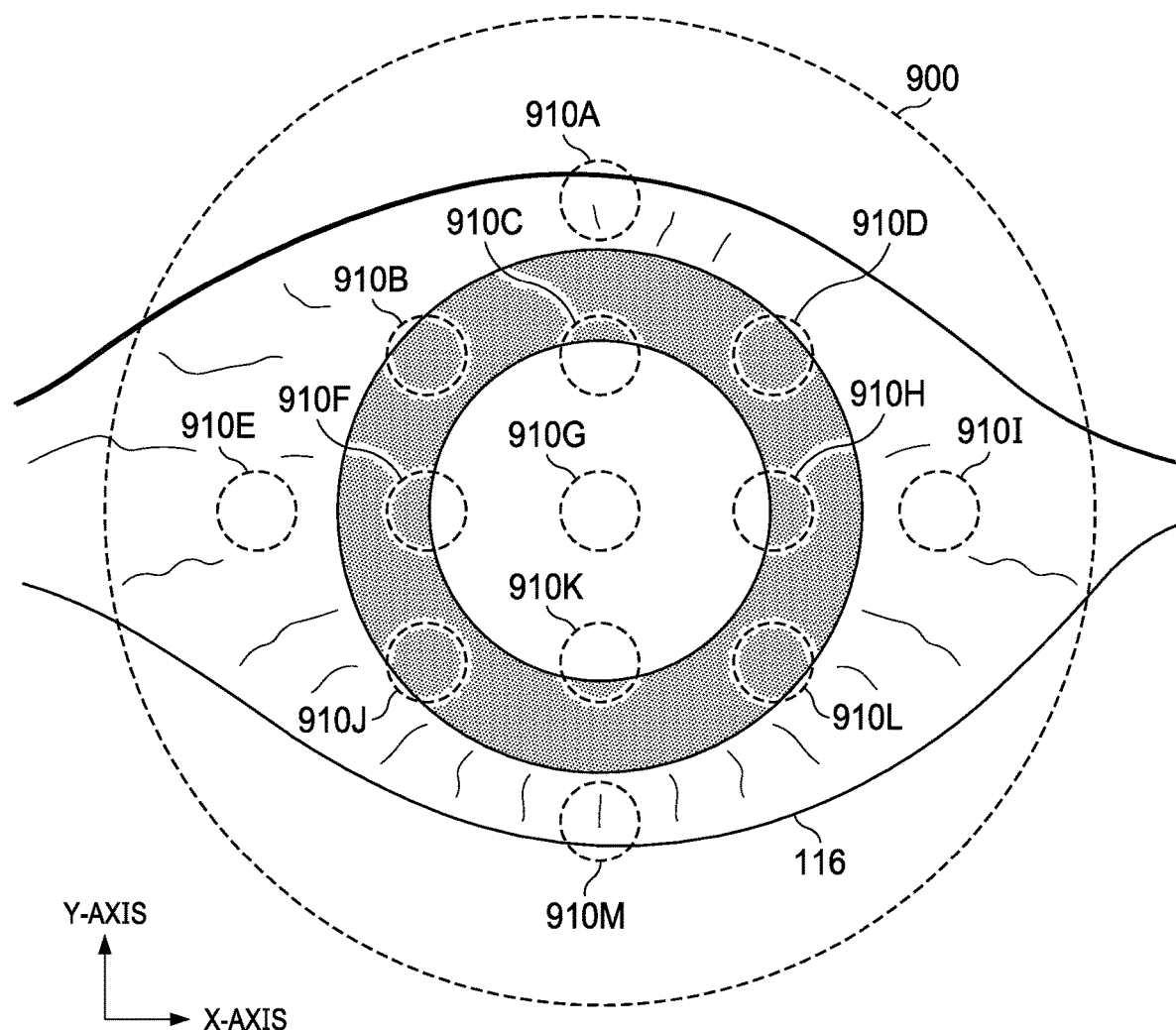
FIG. 9B illustrates an example of multiple positions of a plane that may be utilized with an eye of a patient.
Figure 9C:
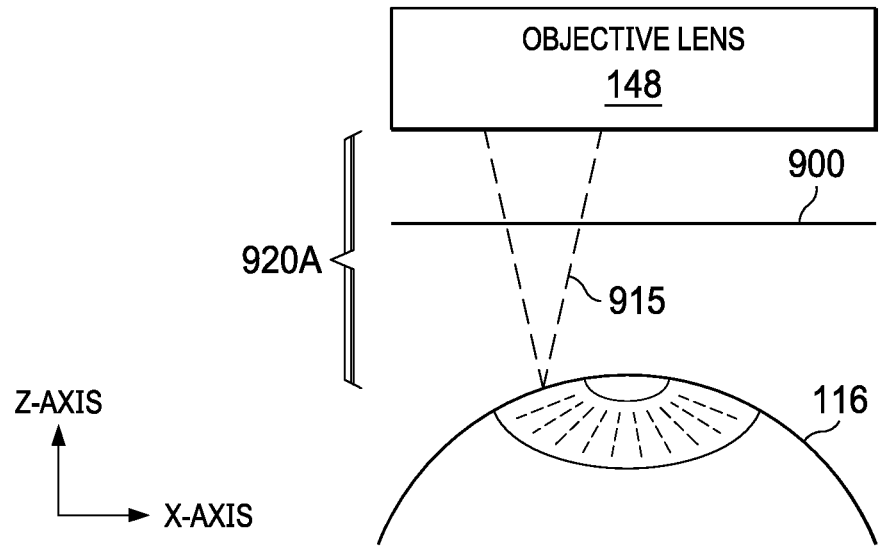
FIGS. 9C-9G illustrate examples of multiple focal point distances of a laser beam.
Figure 9D:
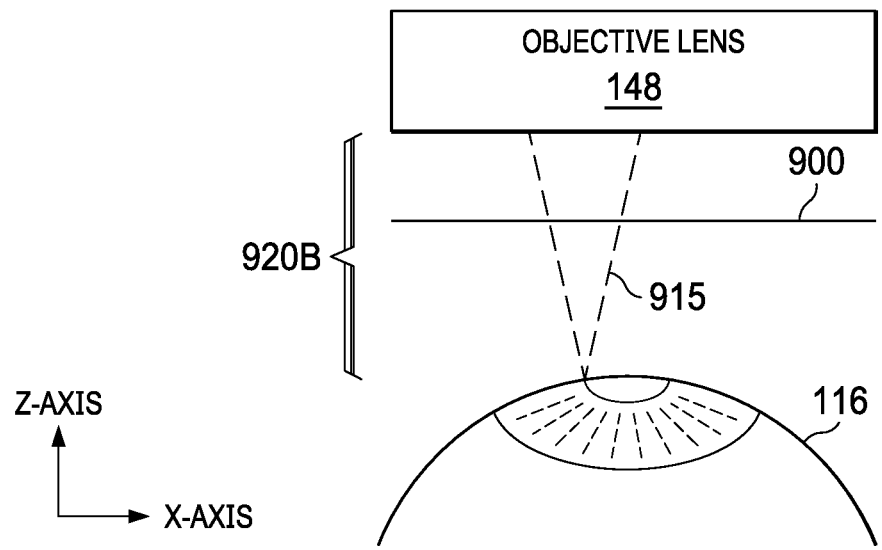
Figure 9E:
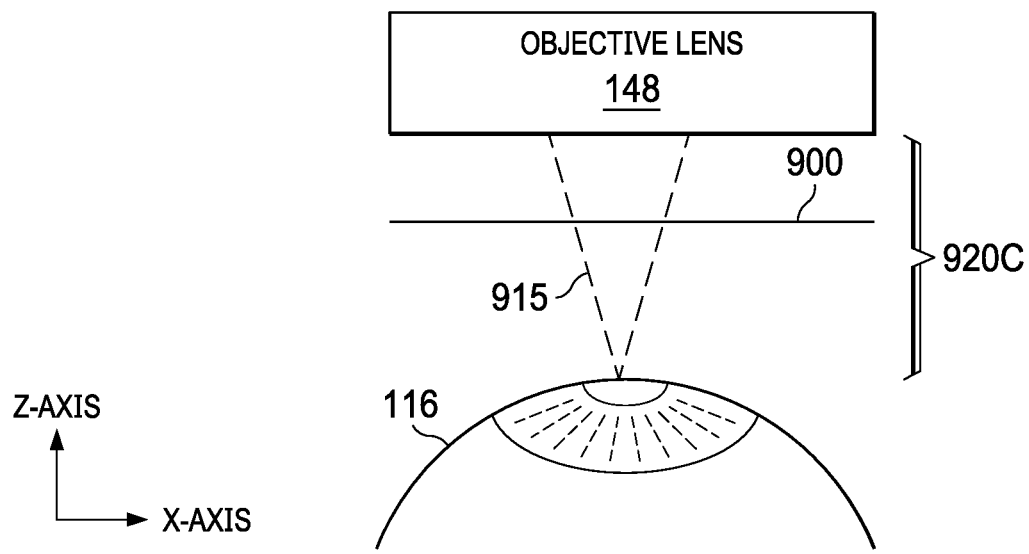
Figure 9F:
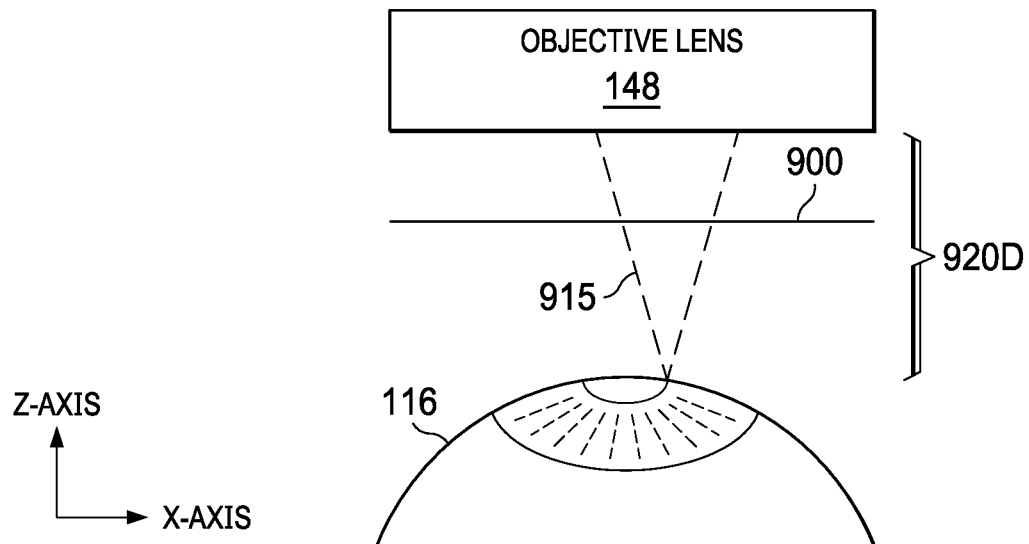
Figure 9G:
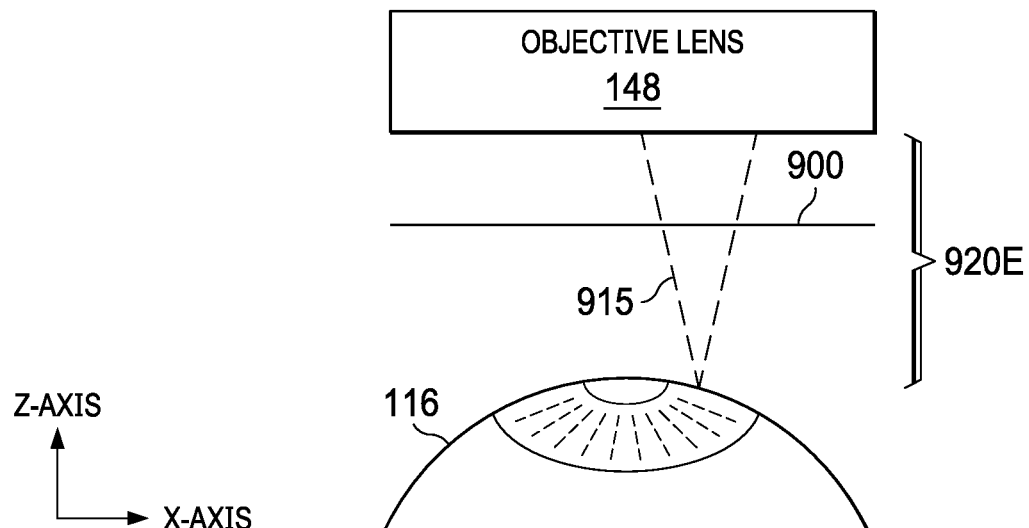
Figure 9H:
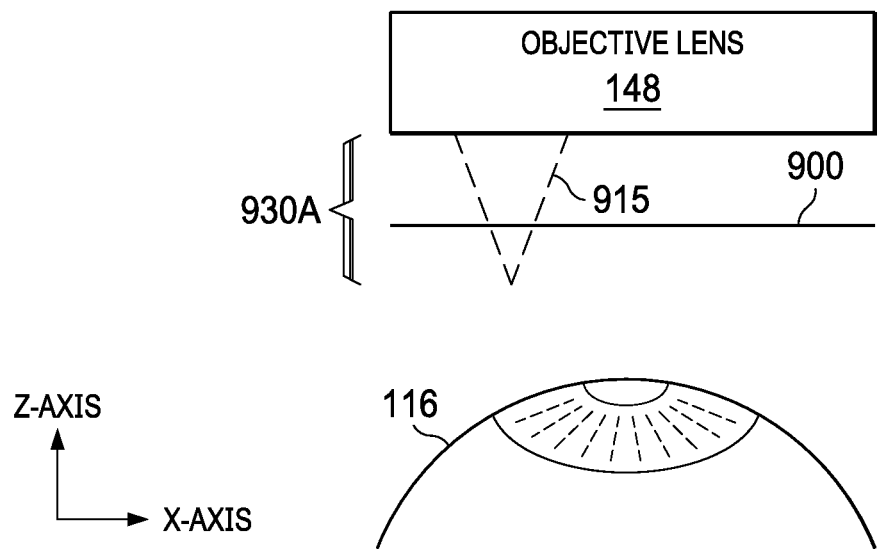
FIGS. 9H-9M illustrate examples of interim focal point distances of a laser beam associated with respective multiple intensity values.
Figure 9I:
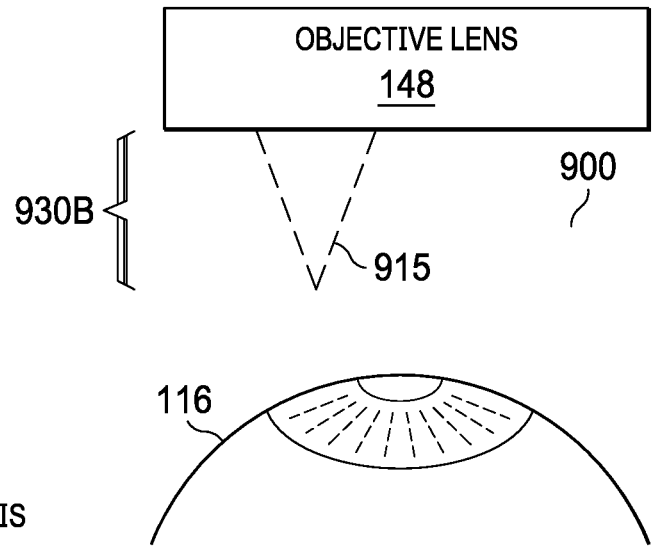
Figure 9J:
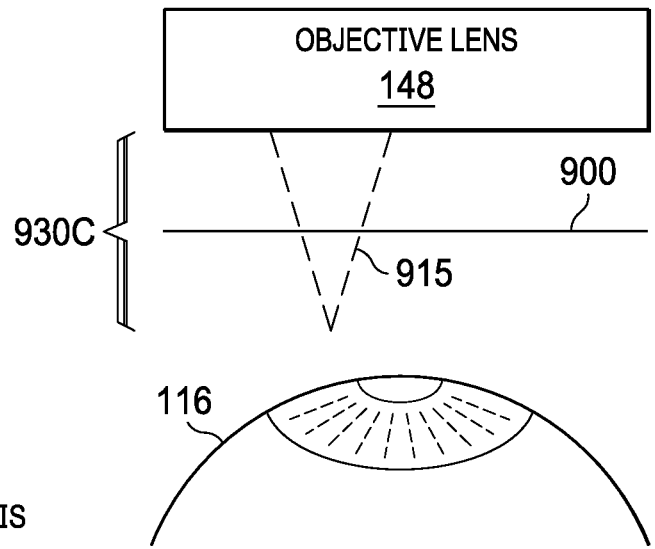

At 704, multiple focal point distances associated with respective multiple positions of a plane orthogonal to the laser beam may be determined. In one example, as illustrated in FIG. 9A, multiple positions 910A-910M of a plane 900, orthogonal to a laser beam, may be associated with multiple focal point distances. Although only fourteen positions are illustrated in FIG. 9A, any number of positions may be utilized. Furthermore, the positions may be at any locations. As shown, plane 900 may be associated with a X-axis and a Y-axis. In a second example, as illustrated in FIG. 9B, multiple positions 910A-910M of plane 900 may be utilized with eye 116. Although only fourteen positions are illustrated in FIG. 9B, any number of positions may be utilized. Furthermore, the positions may be at any locations. In another example, multiple focal point distances 920A-920E of a laser beam 915, illustrated in respective FIGS. 9C-9G, associated with respective multiple positions 910E-910I of plane 900 may be determined. The multiple focal point distances associated with respective multiple positions of the plane orthogonal to the laser beam may be determined via a method illustrated in FIG. 7B.

At 706, a topography of an eye of a patient may be determined based at least on the multiple focal point distances associated with the respective multiple positions. For example, a topography of eye 116 of patient 320 may be determined based at least on the multiple focal point distances associated with the respective multiple positions.

At 708, the topography of the eye of the patient may be displayed. In one example, the topography of the eye of the patient may be displayed via a display. In another example, the topography of the eye of the patient may be displayed via a printer. The printer may print the topography of the eye of on a piece of paper.

Figure 7B:
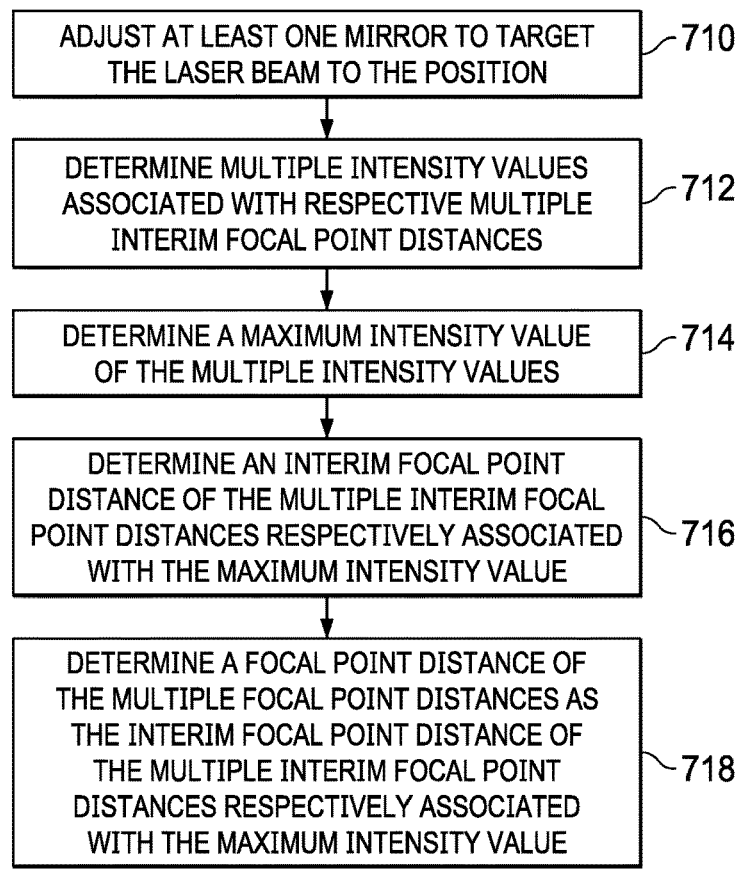
FIG. 7B illustrates an example of method of determining multiple of focal point distances associated with respective multiple positions of a plane orthogonal to a laser beam.

Turning now to FIG. 7B, an example of method of determining multiple of focal point distances associated with respective multiple positions of a plane orthogonal to a laser beam is illustrated. The method illustrated in FIG. 7B may be performed for each position of the multiple positions of the plane orthogonal to the laser beam. For example, the method illustrated in FIG. 7B may be performed for each position of positions 910A-910M of plane 900.

At 710, at least one mirror may be adjusted to target the laser beam to the position of the multiple positions of the plane orthogonal to the laser beam. For example, the at least one mirror may be adjusted to target the laser beam to position 910E of positions 910A-910M of plane 900. Scanner 144 may include one or more mirrors. For example, scanner 144 may target the laser beam to the position of the multiple positions of the plane orthogonal to the laser beam. Scanner 144 may adjust at least one mirror to target the laser beam to the position of the multiple positions of the plane orthogonal to the laser beam.

Figure 9K:
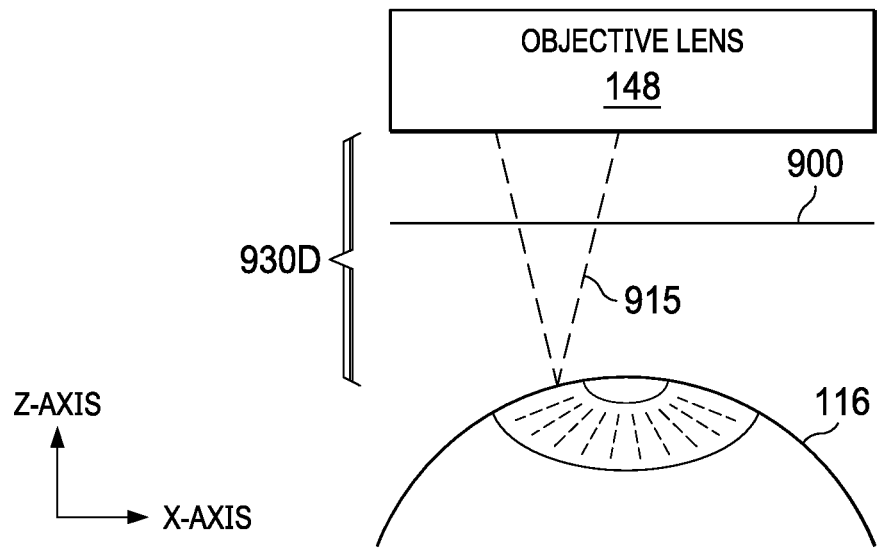
Figure 9L:
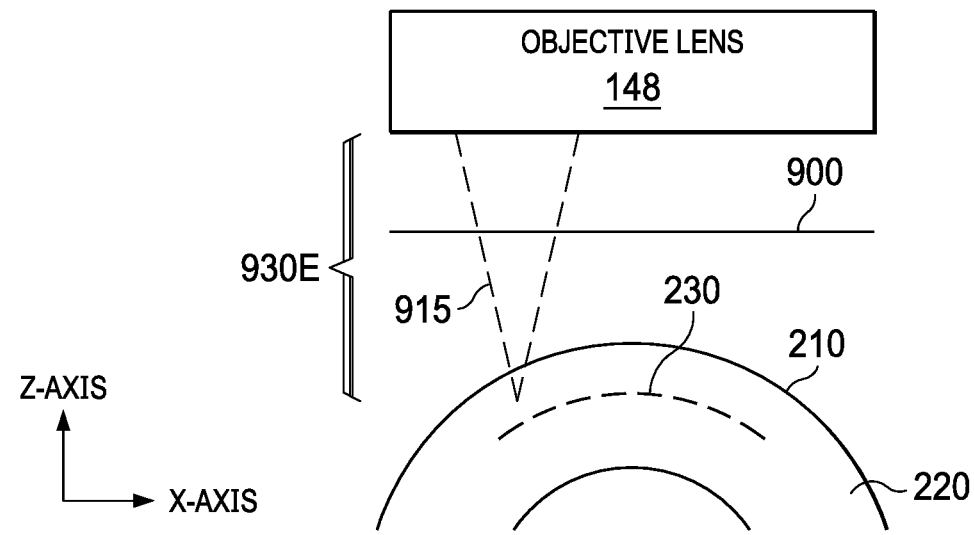
Figure 9M:
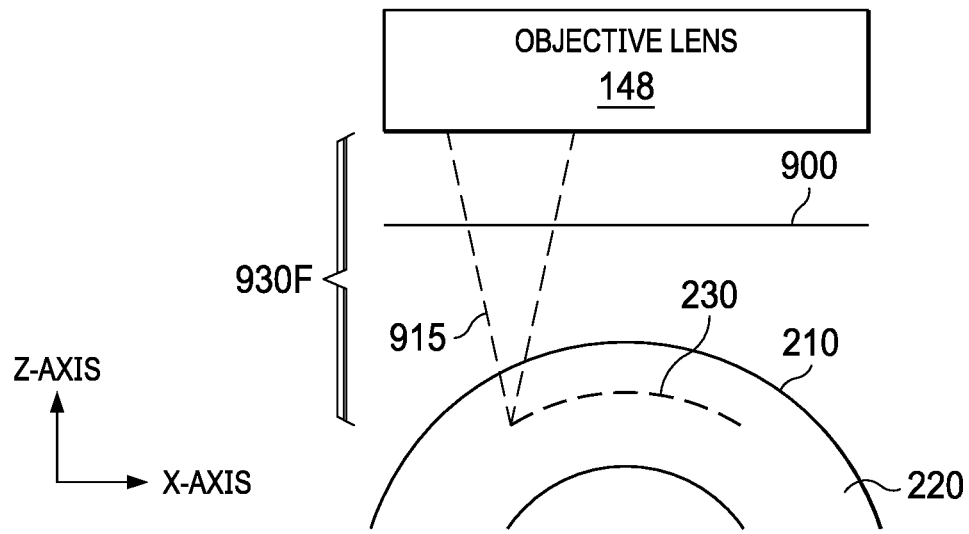
Figure 9N:
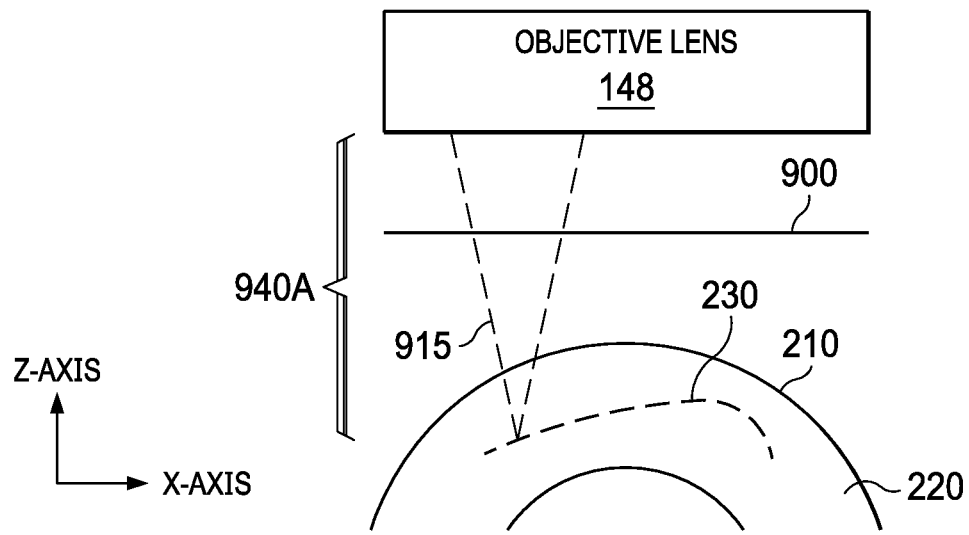
FIGS. 9N-9Q illustrate examples of multiple focal point distances of a laser beam.
Figure 9O:
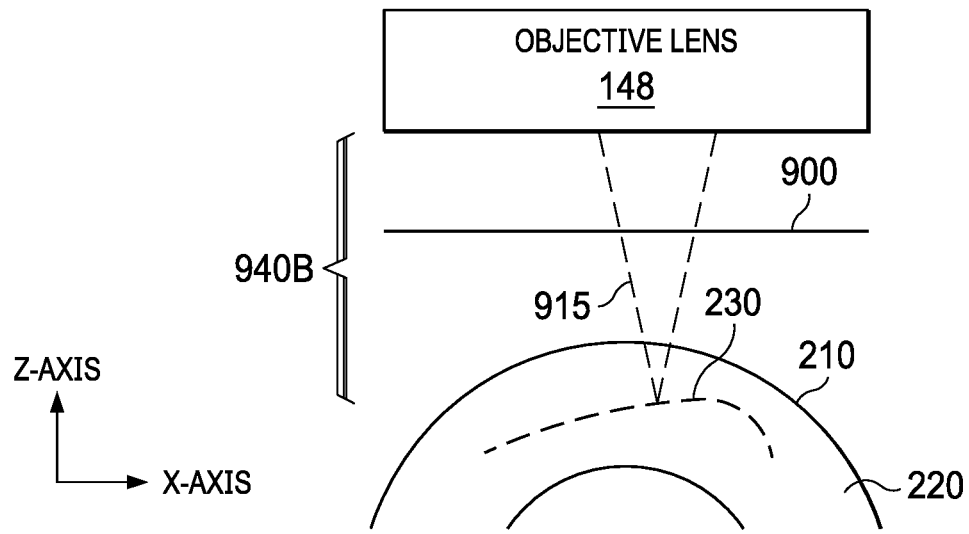
Figure 9P:
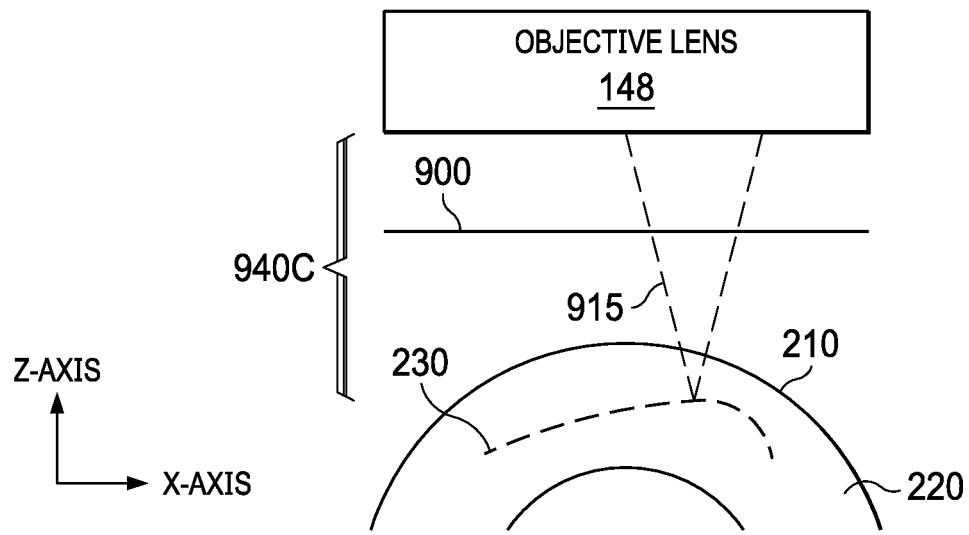
Figure 9Q:
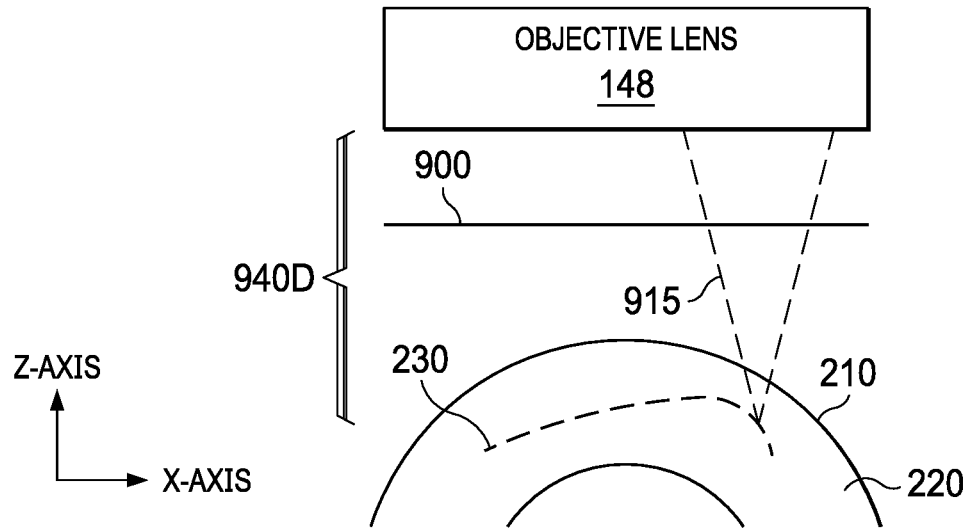

At 712, multiple intensity values associated with respective interim focal point distances may be determined. In one example, multiple intensity values associated with respective interim focal point distances 930A-930D of laser beam 915, respectively illustrated in FIGS. 9H-9K, may be determined. Interim focal point distance 930D of laser beam 915, illustrated in FIG. 9K, may be to a surface 210 of eye 116. In another example, multiple intensity values associated with respective interim focal point distances 930A-930C and 930E of laser beam 915, respectively illustrated in FIGS. 9H-9J, 9L, and 9M, may be determined. Interim focal point distance 930F of laser beam 915, illustrated in FIG. 9M, may be to an incision 230 in eye 116. The multiple intensity values associated with the respective interim focal point distances may be determined via a method illustrated in FIG. 7C.

At 714, a maximum intensity value of the multiple intensity values may be determined. In one example, computer system 152 may determine a maximum intensity value of the multiple intensity values. In another example, computer system 430 may determine a maximum intensity value of the multiple intensity values. If a maximum intensity value associated with interim focal point distance 930D has been determined, another maximum intensity value of the multiple intensity values may be determined. For example, the other maximum intensity value of the multiple intensity values may be associated with interim focal point distance 930F.

At 716, an interim focal point distance of the multiple interim focal point distances respectively associated with the maximum intensity value may be determined. In one example, interim focal point distance 930D of interim focal point distances 930A-930D may be determined. In another example, interim focal point distance 930F of interim focal point distances 930A-930C, 930E, 930F and may be determined. If interim focal point distance 930D has been determined, interim focal point distance 930F may be determined. For example, optical system 110 may utilize additional interim focal point distances 930 that are greater than interim focal point distance 930D in determining another maximum intensity value that is associated with interim focal point distance 930F.

At 718, a focal point distance of the multiple focal point distances may be determined as the interim focal point distance of the multiple interim focal point distances respectively associated with the maximum intensity value. In one example, a focal point distance of the multiple focal point distances may be determined as interim focal point distance 930D, of interim focal point distances 930A-930D, respectively associated with the maximum intensity value. In another example, a focal point distance of the multiple focal point distances may be determined as interim focal point distance 930F, of interim focal point distances 930A-930C, 930E, and 930F, respectively associated with the maximum intensity value.

Figure 7C:
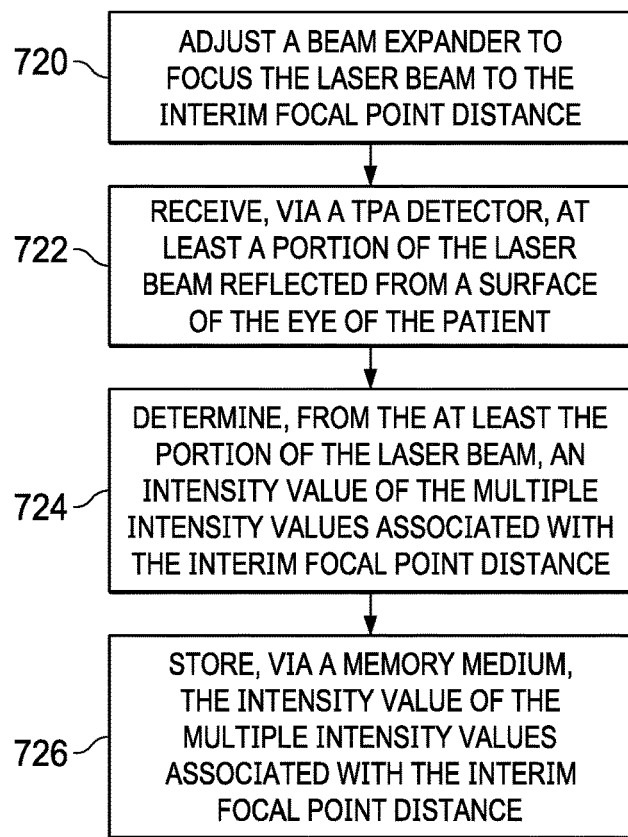
FIG. 7C illustrates an example of a method of determining multiple intensity values associated with respective multiple interim focal point distances.

Turning now to FIG. 7C, an example of a method of determining multiple intensity values associated with respective multiple interim focal point distances is illustrated. The method illustrated in FIG. 7C may be performed for each interim focal point distance of the multiple interim focal point distances. For example, the method illustrated in FIG. 7C may be performed for each interim focal point distance of interim focal point distances 930A-930F.

At 720, a beam expander may be adjusted to focus the laser beam to the interim focal point distance. For example, beam expander 141 may be adjusted to focus the laser beam to interim focal point distance 930. Adjusting beam expander 141 to focus the laser beam to interim focal point distance 930 may include adjusting one or more lenses of beam expander 141. For example, one or more of lenses 142A and 142B may be adjusted to focus the laser beam to an interim focal point distance 930.

At 722, at least a portion of the laser beam reflected from a surface of an eye of a patient may be received via a TPA. For example, TPA detector 130 may receive at least a portion of the laser beam reflected from surface 210 of eye 116 of patient 320.

At 724, an intensity value, of the multiple intensity values, associated with the interim focal point distance may be determined from the at least the portion of the laser beam. For example, an intensity value associated with an interim focal point distance 930 may be determined. An intensity value associated with interim focal point distance 930D may be a maximum intensity value. An intensity value associated with interim focal point distance 930F may be a maximum intensity value.

Determining, from the at least the portion of the laser beam, an intensity value of the multiple intensity values associated with the interim focal point distance may include an ADC receiving an analog signal from the TPA detector. Determining, from the at least the portion of the laser beam, an intensity value of the multiple intensity values associated with the interim focal point distance may include the ADC converting the analog signal from the TPA detector to the intensity value of the multiple intensity values associated with the interim focal point distance. In one example, the ADC may convert current into digital values. In another example, the ADC may convert voltage into digital values.

At 726, the intensity value, of the multiple intensity values, associated with the interim focal point distance may be stored via a memory medium. For example, the intensity value associated with the interim focal point distance and the interim focal point distance may be stored via the memory medium. The interim focal point distance may be accessed and/or may be retrieved from the memory medium via the intensity value associated with the interim focal point distance. For example, a focal point distance may be accessed and/or may be retrieved from the memory medium via a maximum intensity value.

Storing the intensity value associated with the interim focal point distance and the interim focal point distance via the memory medium may include storing the intensity value associated with the interim focal point distance and the interim focal point distance via a database. The interim focal point distance may be accessed and/or may be retrieved from the database via the intensity value associated with the interim focal point distance. For example, a focal point distance may be accessed and/or may be retrieved from the database via a maximum intensity value. The database may be stored locally, via a remote computer system, or via a remote data center. In one example, the database may include a relational database. In a second example, the database may include a graph database. In a third example, the database may include an associative array. In another example, the database may include a NoSQL database.

Figure 7D:
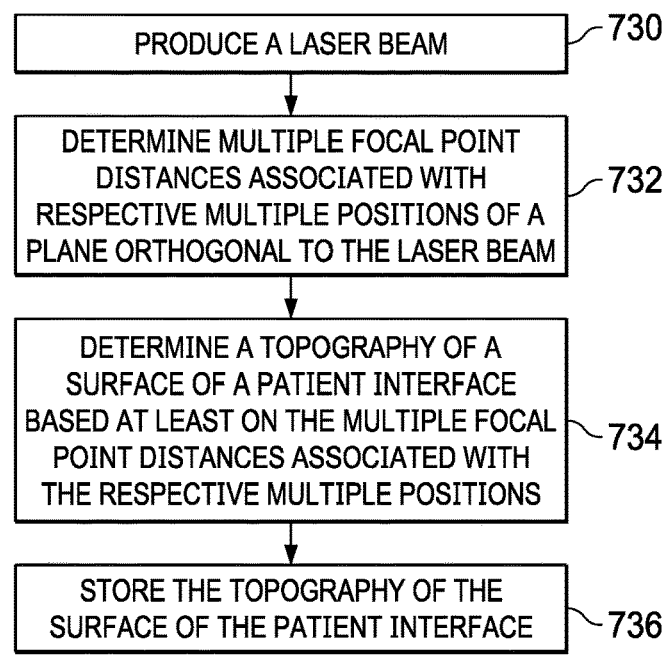
FIG. 7D illustrates an example of a method of determining a topography of a portion of a patient interface.

Turning now to FIG. 7D, an example of a method of determining a topography of a portion of a patient interface is illustrated. At 730, a laser beam may be produced. For example, laser 120 may produce a laser beam. Producing a laser beam may include pulsing the laser beam. Pulsing the laser beam may include pulsing the laser beam at femtosecond pulse durations. The laser beam may include photons associated with multiple frequencies.

Figure 10A:
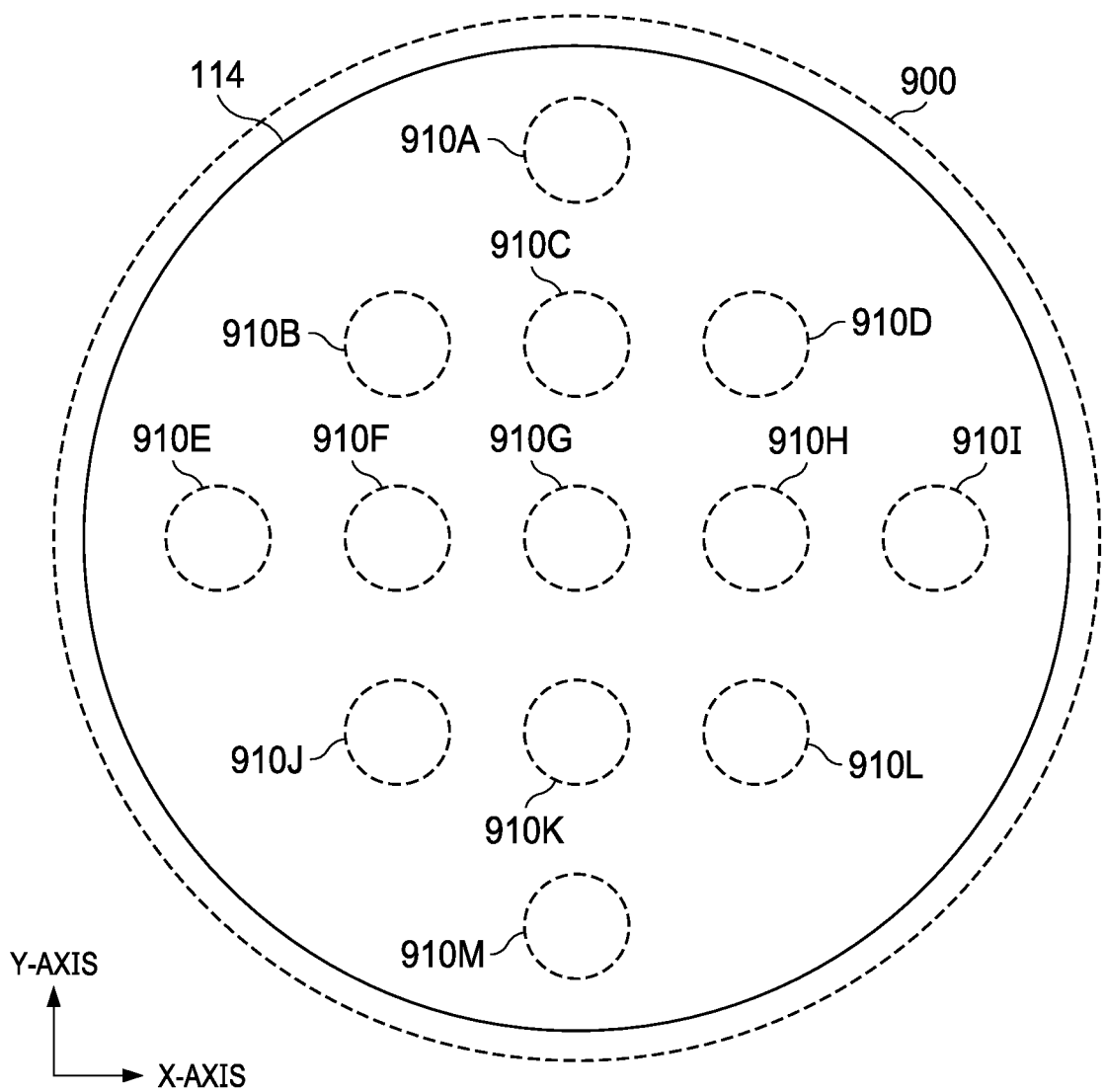
FIG. 10A illustrates an example of multiple positions of a plane utilized with a patient interface.
Figure 10B:
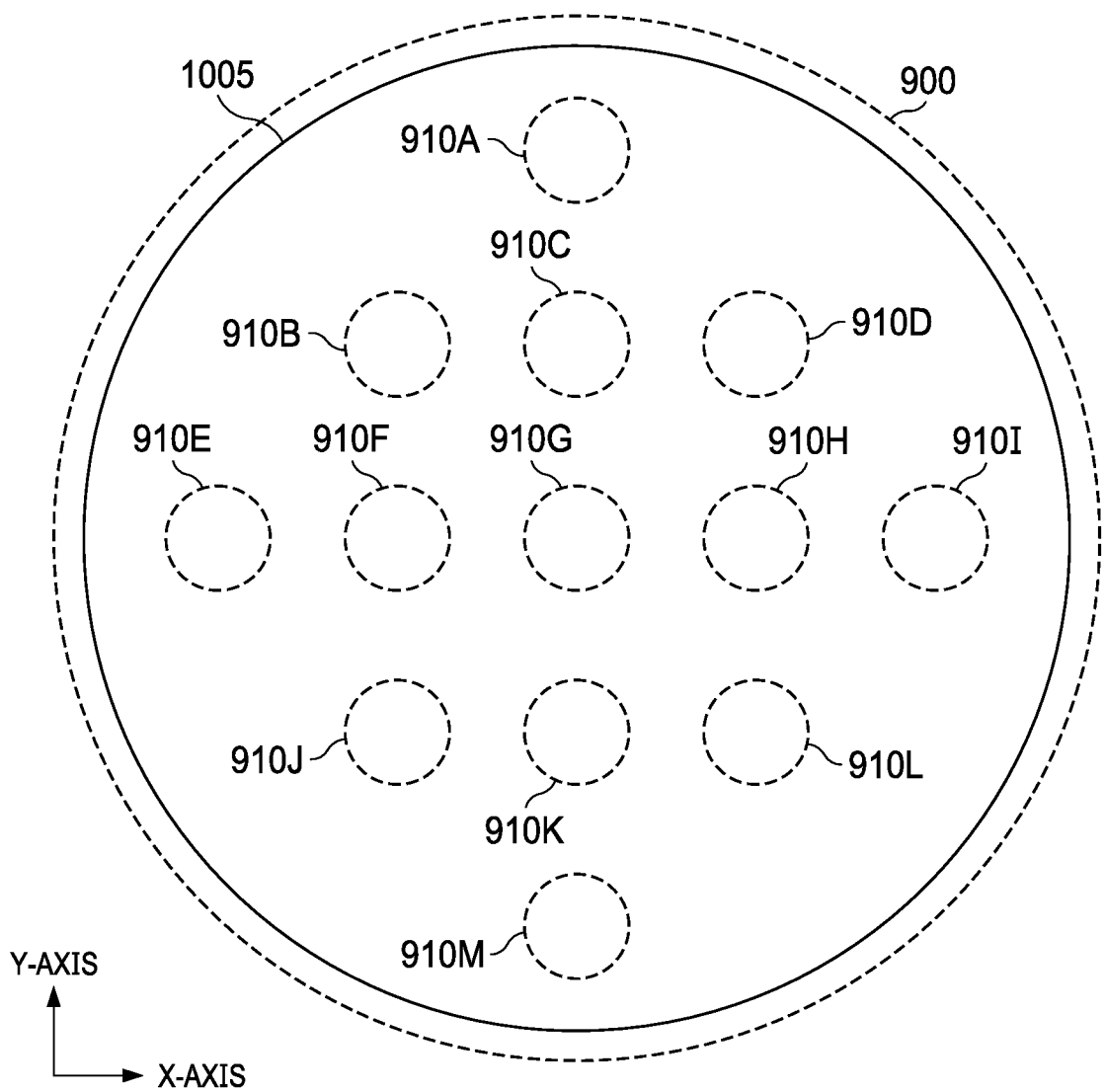
FIG. 10B illustrates an example of multiple positions of a plane utilized with a surface of a patient interface.
Figure 10C:
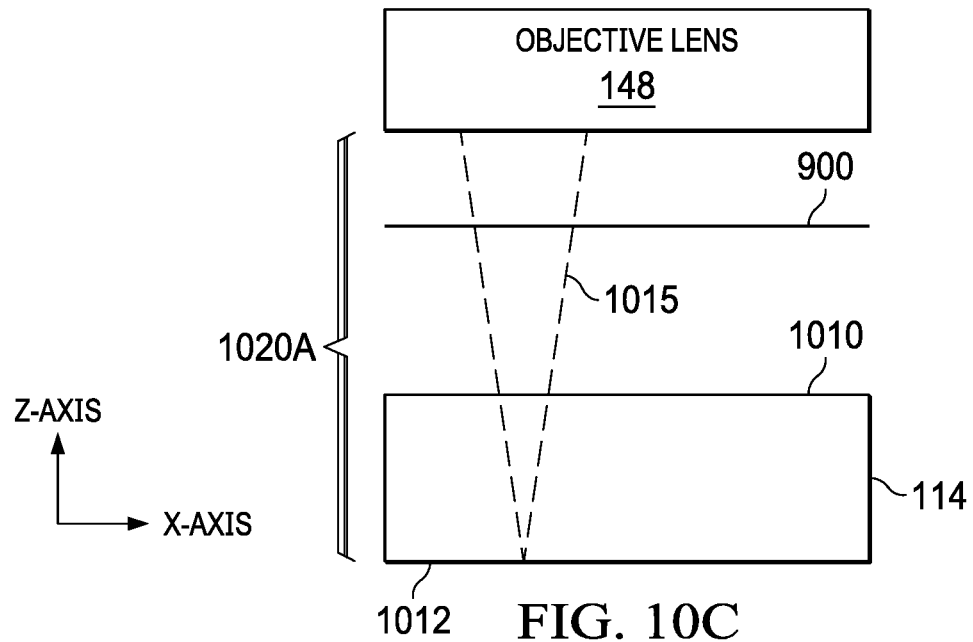
FIGS. 10C-10G illustrate examples of multiple focal point distances of a laser beam.
Figure 10D:
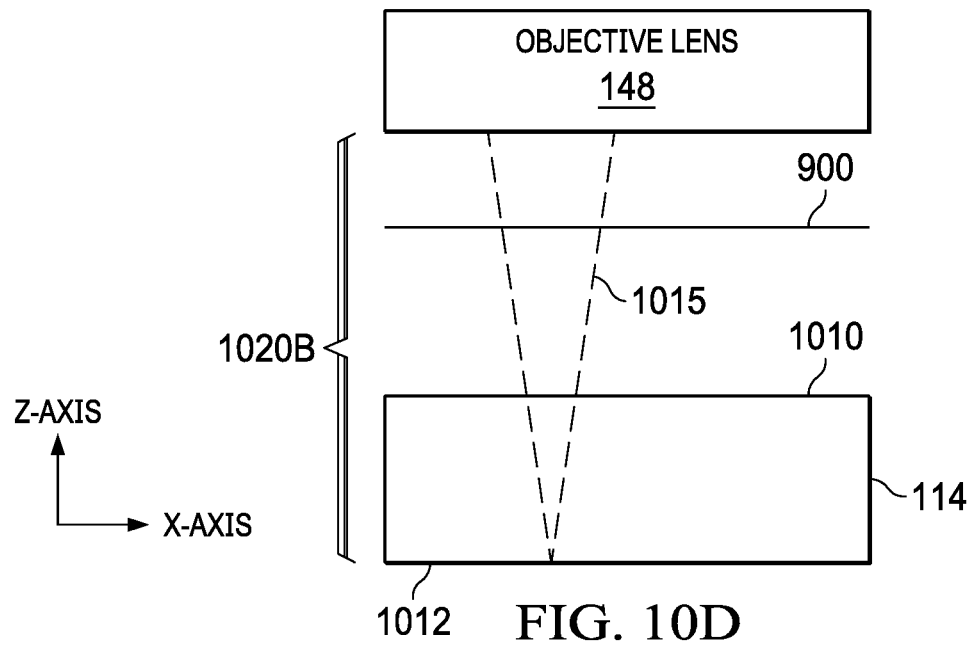

At 732, multiple focal point distances associated with respective multiple positions of a plane orthogonal to the laser beam may be determined. In one example, as illustrated in FIG. 9A, multiple positions 910A-910M of a plane 900, orthogonal to a laser beam, may be associated with multiple focal point distances. Although only fourteen positions are illustrated in FIG. 9A, any number of positions may be utilized. Furthermore, the positions may be at any locations. As shown, plane 900 may be associated with a X-axis and a Y-axis. In a second example, as illustrated in FIG. 10A, multiple positions 910A-910M of plane 900 may be utilized with patient interface 114. Although only fourteen positions are illustrated in FIG. 10A, any number of positions may be utilized. Furthermore, the positions may be at any locations. In another example, as illustrated in FIG. 10B, multiple positions 910A-910M of plane 900 may be utilized with a surface 1005 of patient interface 114. Although only fourteen positions are illustrated in FIG. 10B, any number of positions may be utilized. Furthermore, the positions may be at any locations.

Figure 10E:
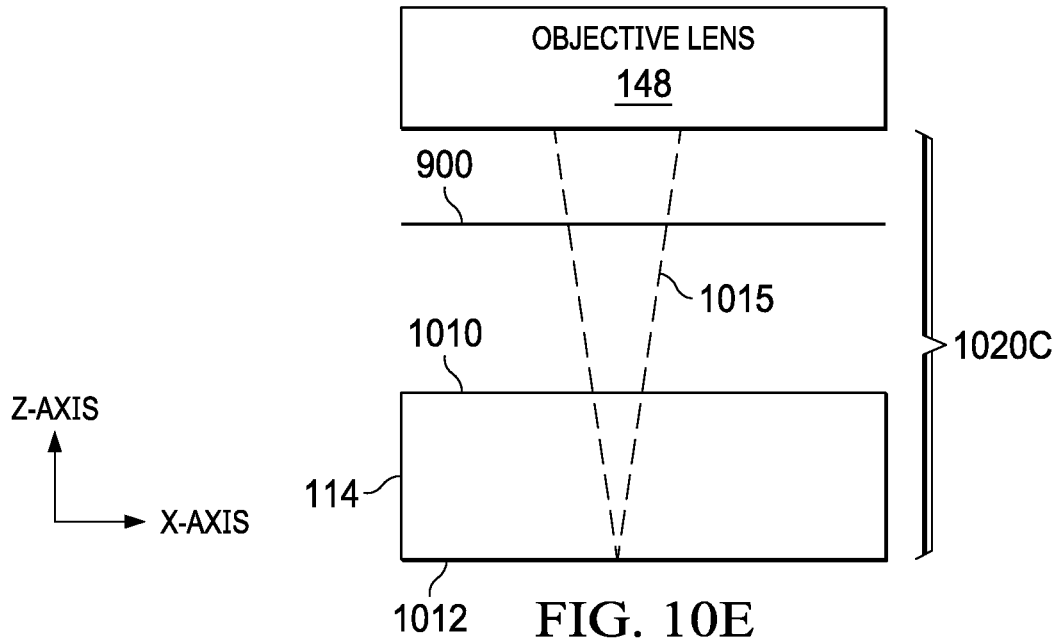
Figure 10F:
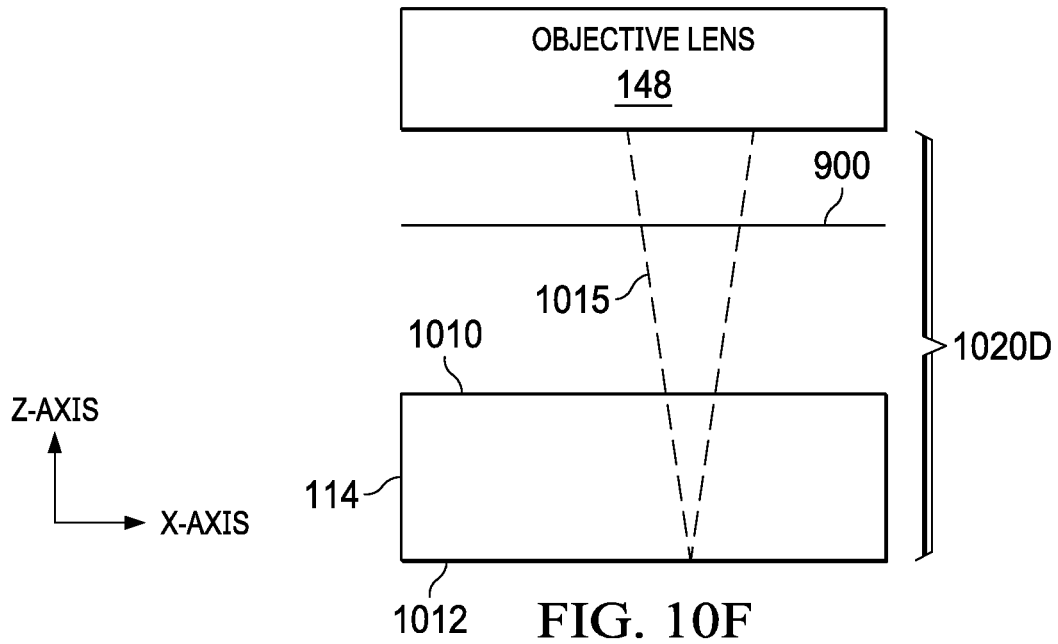
Figure 10G:
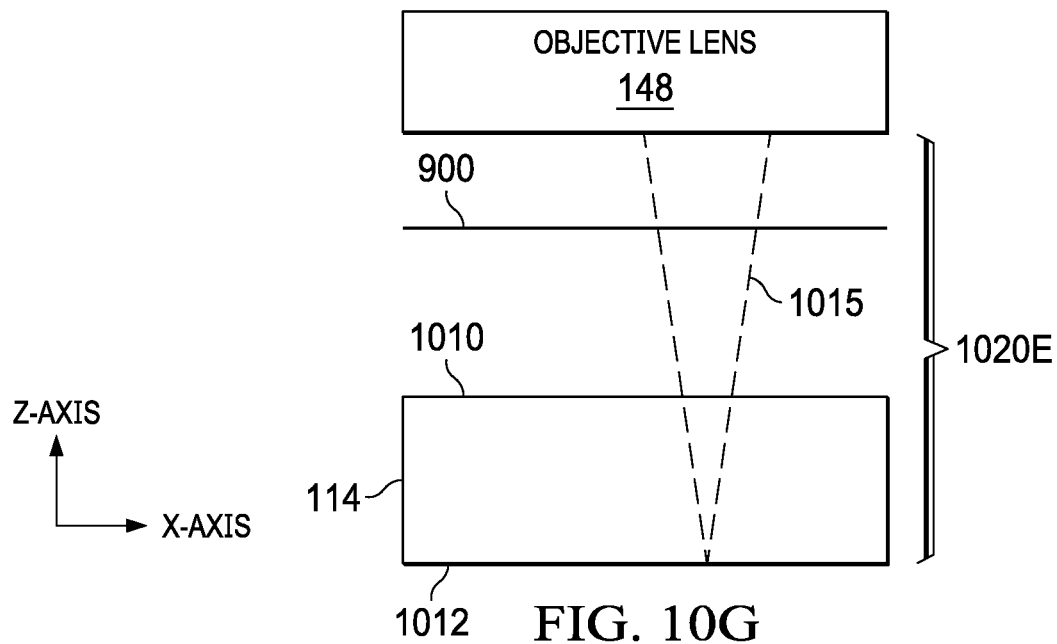
Figure 10H:
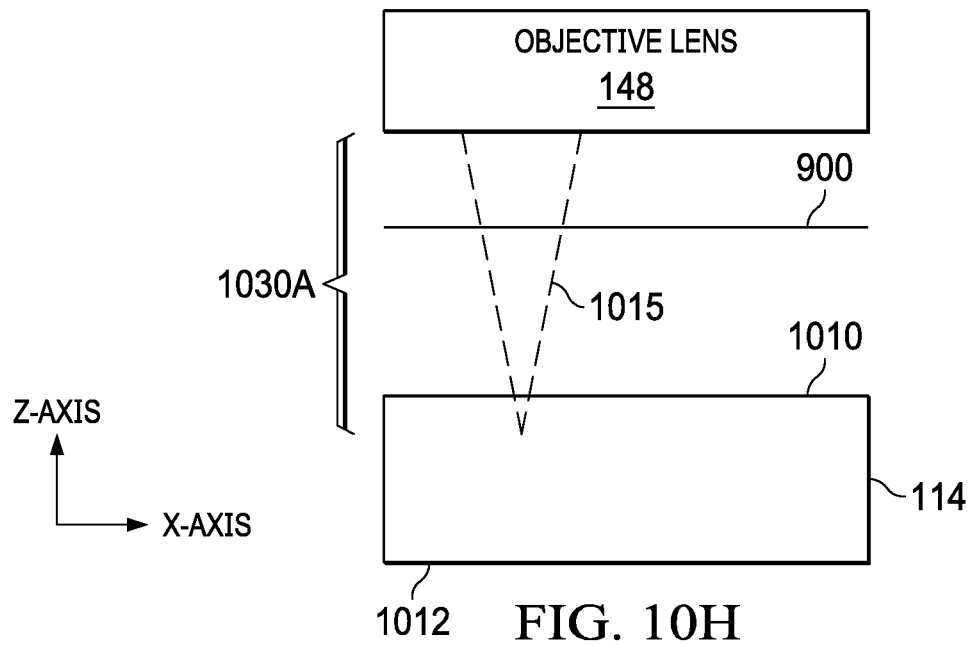
FIGS. 10H-10K illustrate examples of interim focal point distances of a laser beam associated with respective multiple intensity values.
Figure 10I:
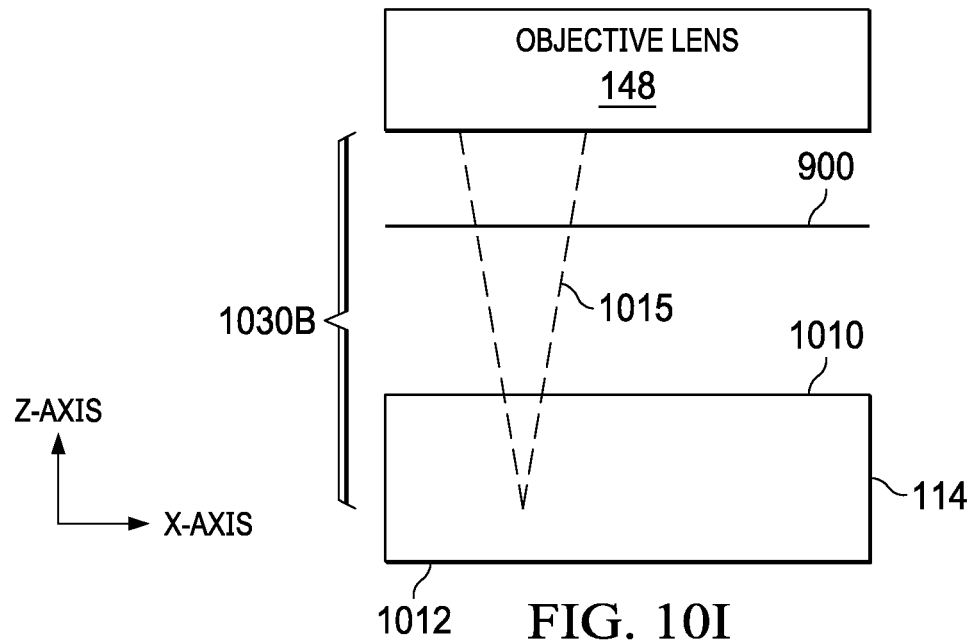
Figure 10J:
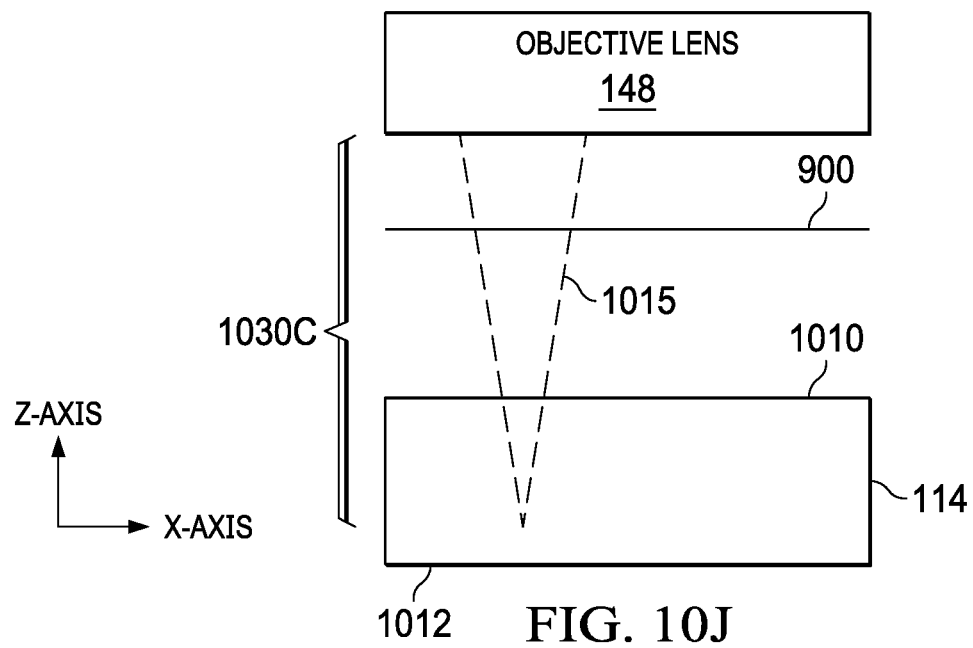
Figure 10K:
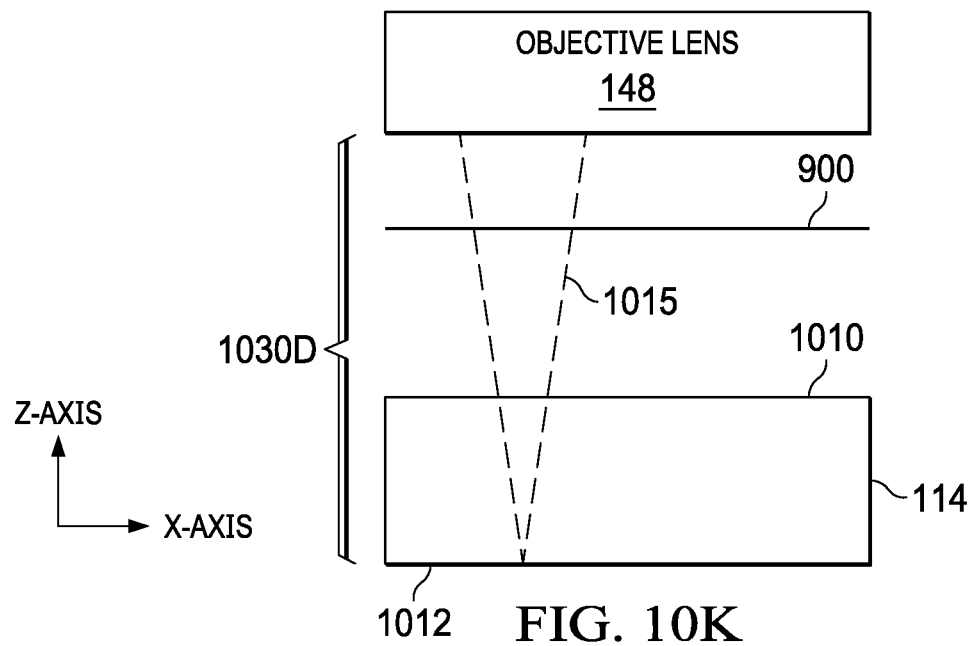

At 734, a topography of a surface of a patient interface may be determined based at least on the multiple focal point distances associated with the respective multiple positions. For example, a topography of a surface 1005 of patient interface 114 may be determined based at least on the multiple focal point distances associated with the respective multiple positions. Surface 1005 may be a surface 1012 as illustrated in FIGS. 10E-10G. As an example, multiple focal point distances 1020A-1020E (respectively illustrated in FIGS. 10C-10G) may be associated with respective multiple positions 910E-910I.

At 736, the topography of the surface of the patient interface may be stored. For example, the topography of the surface of the patient interface may be stored via a memory medium. Storing the topography of the surface of the patient interface via the memory medium may include storing the topography of the surface of the patient interface via a database. The topography of the surface of the patient interface may be accessed and/or may be retrieved from the database. The database may be stored locally, via a remote computer system, or via a remote data center. In one example, the database may include a relational database. In a second example, the database may include a graph database. In a third example, the database may include an associative array. In another example, the database may include a NoSQL database.

Figure 7E:
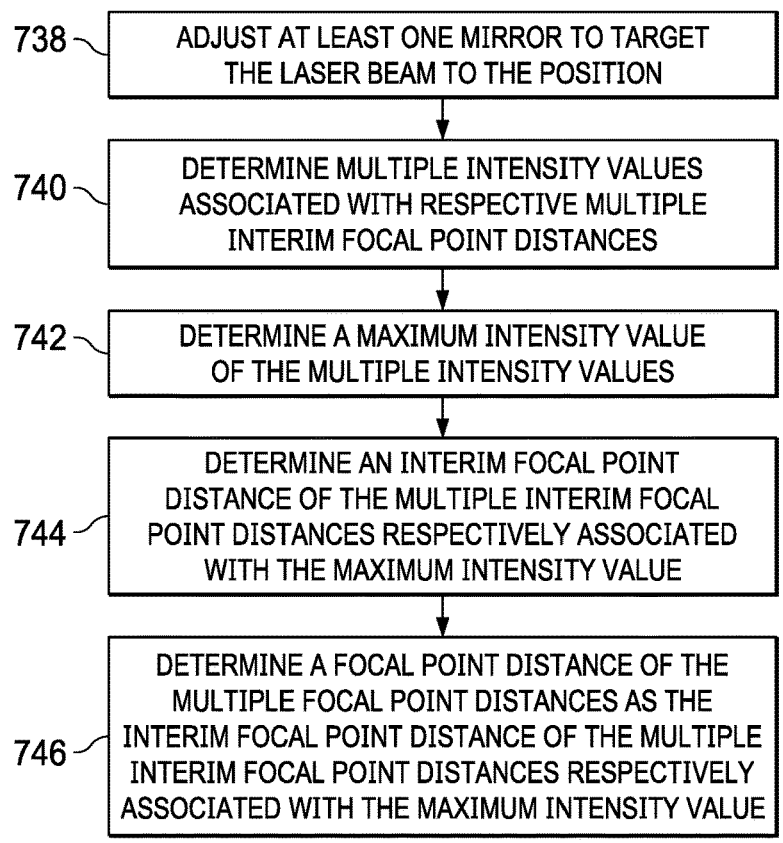
FIG. 7E illustrates another example of method of determining multiple of focal point distances associated with respective multiple positions of a plane orthogonal to a laser beam.

Turning now to FIG. 7E, another example of method of determining multiple of focal point distances associated with respective multiple positions of a plane orthogonal to a laser beam is illustrated. The method illustrated in FIG. 7E may be performed for each position of the multiple positions of the plane orthogonal to the laser beam. For example, the method illustrated in FIG. 7E may be performed for each position of positions 910A-910M of plane 900.

At 738, at least one mirror may be adjusted to target the laser beam to the position of the multiple positions of the plane orthogonal to the laser beam. For example, the at least one mirror may be adjusted to target the laser beam to position 910E of positions 910A-910M of plane 900. Scanner 144 may include one or more mirrors. For example, scanner 144 may target the laser beam to the position of the multiple positions of the plane orthogonal to the laser beam. Scanner 144 may adjust at least one mirror to target the laser beam to the position of the multiple positions of the plane orthogonal to the laser beam.

At 740, multiple intensity values associated with respective interim focal point distances may be determined. For example, multiple intensity values associated with respective interim focal point distances 1030A-1030D of a laser beam 1015, respectively illustrated in FIGS. 10H-10K, may be determined. Interim focal point distance 1030D of laser beam 1015, illustrated in FIG. 10K, may be to a surface or end 1012 of a patient interface 114. Although surface or end 1012 of patient interface 114 is illustrated as linear or "flat", surface or end 1012 of patient interface 114 may be non-linear. For example, surface or end 1012 of patient interface 114 may be concave or convex. As shown in FIGS. 10A-10K, patient interface may have surfaces 1010 and 1012. Surface 1010 may be an anterior surface or an anterior end of patient interface 114. Surface 1012 may be a posterior surface or a posterior end of patient interface 114. In one example, surface 1012 may be surface 1005. In a second example, surface 1012 may be surface 112. In another example, surface 1012 may be a surface of lens 486. Surface 1012 may be a surface of lens 486 that contacts eye 116.

At 742, a maximum intensity value of the multiple intensity values may be determined. For example, computer system 152 may determine a maximum intensity value of the multiple intensity values. In another example, computer system 430 may determine a maximum intensity value of the multiple intensity values.

At 744, an interim focal point distance of the multiple interim focal point distances respectively associated with the maximum intensity value may be determined. For example, interim focal point distance 1030D of interim focal point distances 1030A-1030D may be determined.

At 746, a focal point distance of the multiple focal point distances may be determined as the interim focal point distance of the multiple interim focal point distances respectively associated with the maximum intensity value. In one example, a focal point distance of the multiple focal point distances may be determined as interim focal point distance 1030D, of interim focal point distances 1030A-1030D, respectively associated with the maximum intensity value.

Figure 7F:
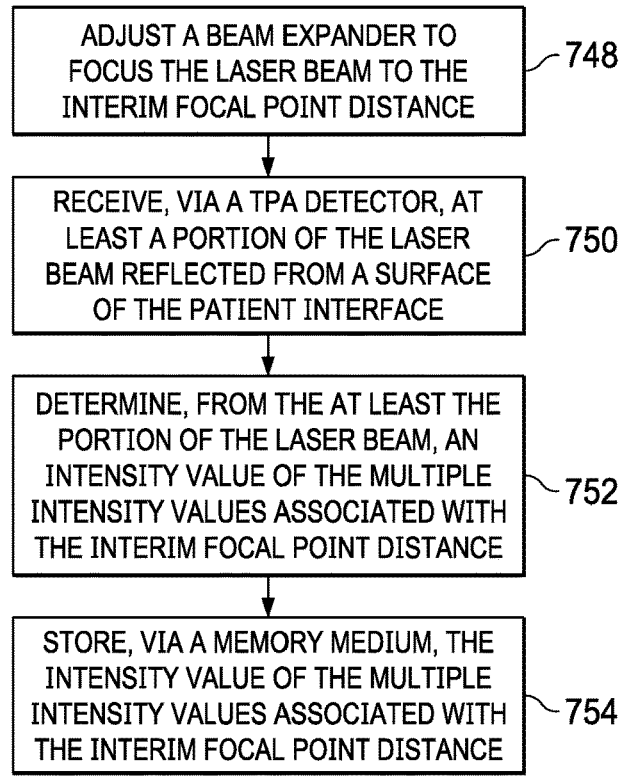
FIG. 7F illustrates another example of a method of determining multiple intensity values associated with respective multiple interim focal point distances.

Turning now to FIG. 7F, another example of a method of determining multiple intensity values associated with respective multiple interim focal point distances is illustrated. The method illustrated in FIG. 7F may be performed for each interim focal point distance of the multiple interim focal point distances. For example, the method illustrated in FIG. 7F may be performed for each interim focal point distance of interim focal point distances 1030A-1030D.

At 748, a beam expander may be adjusted to focus the laser beam to the interim focal point distance. For example, beam expander 141 may be adjusted to focus the laser beam to interim focal point distance 1030. Adjusting beam expander 141 to focus the laser beam to interim focal point distance 1030 may include adjusting one or more lenses of beam expander 141. For example, one or more of lenses 142A and 142B may be adjusted to focus the laser beam to an interim focal point distance 1030.

At 750, at least a portion of the laser beam reflected from a surface of a patient interface may be received via a TPA. For example, TPA detector 130 may receive at least a portion of the laser beam reflected from surface 1012 of patient interface 114.

At 752, an intensity value, of the multiple intensity values, associated with the interim focal point distance may be determined from the at least the portion of the laser beam. For example, an intensity value associated with an interim focal point distance 1030 may be determined. An intensity value associated with interim focal point distance 1030D may be a maximum intensity value.

Determining, from the at least the portion of the laser beam, an intensity value of the multiple intensity values associated with the interim focal point distance may include an ADC receiving an analog signal from the TPA detector. Determining, from the at least the portion of the laser beam, an intensity value of the multiple intensity values associated with the interim focal point distance may include the ADC converting the analog signal from the TPA detector to the intensity value of the multiple intensity values associated with the interim focal point distance. In one example, the ADC may convert current into digital values. In another example, the ADC may convert voltage into digital values.

At 754, the intensity value, of the multiple intensity values, associated with the interim focal point distance may be stored via a memory medium. For example, the intensity value associated with the interim focal point distance and the interim focal point distance may be stored via the memory medium. The interim focal point distance may be accessed and/or may be retrieved from the memory medium via the intensity value associated with the interim focal point distance. For example, a focal point distance may be accessed and/or may be retrieved from the memory medium via a maximum intensity value.

Storing the intensity value associated with the interim focal point distance and the interim focal point distance via the memory medium may include storing the intensity value associated with the interim focal point distance and the interim focal point distance via a database. The interim focal point distance may be accessed and/or may be retrieved from the database via the intensity value associated with the interim focal point distance. For example, a focal point distance may be accessed and/or may be retrieved from the database via a maximum intensity value. The database may be stored locally, via a remote computer system, or via a remote data center. In one example, the database may include a relational database. In a second example, the database may include a graph database. In a third example, the database may include an associative array. In another example, the database may include a NoSQL database.

The multiple intensity values may be utilized to determine a topography. For example, the multiple intensity values may be utilized to determine a topography of a surface of a patient interface. The multiple intensity values may be utilized to determine a topography of surface 1012 of patient interface 114. For example, a surface of patient interface 114 may include manufacturing inconsistencies and/or manufacturing flaws. When eye 116 is in contact with surface 1012 of patient interface 114, the topography of surface 1012 may be utilized in determining and/or maintaining a depth of a cut or incision in eye 116. For example, the topography of surface 1012 may be utilized as a topography of a surface of eye 116 in determining and/or maintaining a depth of a cut or incision in eye 116 when eye 116 is in contact with surface 1012.

Figure 8A:
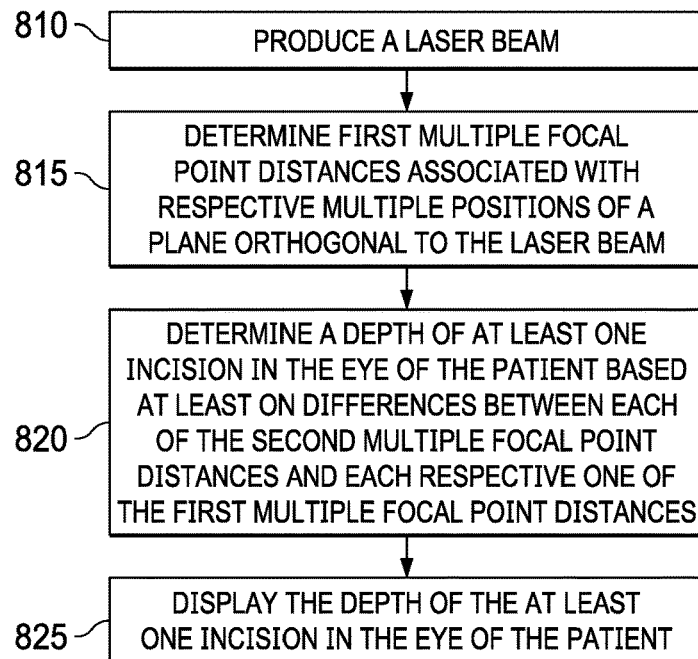
FIG. 8A, illustrates an example of a method of determining at least one incision depth.

Turning now to FIG. 8A, an example of a method of determining at least one incision depth is illustrated. At 810, a laser beam may be produced. For example, laser 120 may produce a laser beam. Producing a laser beam may include pulsing the laser beam. Pulsing the laser beam may include pulsing the laser beam at femtosecond pulse durations. The laser beam may include photons associated with multiple frequencies.

At 815, first multiple focal point distances associated with respective multiple positions of a plane orthogonal to the laser beam may be determined. In one example, as illustrated in FIG. 9A, multiple positions 910A-910M of plane 900, orthogonal to a laser beam, may be associated with multiple focal point distances. Although only fourteen positions are illustrated in FIG. 9A, any number of positions may be utilized. Further, the positions may be at any locations. As shown, plane 900 may be associated with a X-axis and a Y-axis. In a second example, as illustrated in FIG. 9B, multiple positions 910A-910M of plane 900 may be utilized with eye 116. Although only fourteen positions are illustrated in FIG. 9B, any number of positions may be utilized. Further, the positions may be at any locations. In another example, multiple focal point distances 940A-940D of laser beam 915, illustrated in respective FIGS. 9N-9Q, associated with respective multiple positions 910E-910H of plane 900 may be determined. The multiple focal point distances associated with respective multiple positions of the plane orthogonal to the laser beam may be determined via a method illustrated in FIG. 8B.

At 820, a depth of at least one incision in the eye of the patient may be determined based at least on differences between each of second multiple focal point distances and each respective one of the first multiple focal point distances. In one example, a depth of incision 230 in eye 116 of patient 320 may be determined based at least on differences between focal point distances 940A-940D and respective focal point distances 920A-920D. The second multiple focal point distances may be associated with a topography of a surface of eye 116. In a second example, a depth of incision 230 in eye 116 of patient 320 may be determined based at least on differences between focal point distances 940A-940D and respective focal point distances 1020A-1020D. The second multiple focal point distances may be associated with a topography of a surface of patient interface 114. In another example, a depth of incision 230 in eye 116 of patient 320 may be determined based at least on differences between focal point distances 942A-942D, respectively illustrated in FIGS. 9U-9X, and respective focal point distances 920A-920D.

A topography of the at least one incision in the eye of the patient may be determined based at least on differences between each of the second multiple focal point distances and each respective one of the first multiple focal point distances. A flap thickness may be determined via the depth of the at least one incision in the eye of the patient. For example, a flap thickness profile may be determined based at least on one or more depths of at least one incision in the eye of the patient. A flap thickness may be determined based at least on differences between each of the second multiple focal point distances and each respective one of the first multiple focal point distances.

A cutting depth may be corrected based at least on a depth of an incision in the eye of the patient. In one example, a cutting depth may be maintained (e.g., with little deviations or no deviations from a prescribed cutting depth) while an incision in the eye of the patient is being performed. In a second example, a cutting contour may be maintained (e.g., with little deviations or no deviations from a prescribed cutting depth) while an incision in the eye of the patient is being performed. A little deviation from a prescribed cutting depth may be a margin of acceptable error for the prescribed cutting depth. In a third example, a flap may be incised in the eye of the patient with little deviation or no deviation from a prescribed cutting depth. In another example, a lenticule may be incised in the eye of the patient with little deviation or no deviation from a prescribed cutting depth. As an example, a WAVELIGHT® FS 200 laser system, available from Alcon Vision LLC, may perform an incision in the eye of the patient.

At 825, the depth of the at least one incision in the eye of the patient may be displayed. In one example, the depth of the at least one incision may be displayed via a display. In another example, the depth of the at least one incision may be displayed via a printer. The printer may print the depth of the at least one incision on a piece of paper. The topography of the eye of the patient may be displayed with the depth of the at least one incision in the eye of the patient. The topography of the surface of the patient interface may be displayed with the depth of the at least one incision in the eye of the patient. The topography of the at least one incision in the eye of the patient may be displayed. The topography of the eye of the patient and the topography of the at least one incision in the eye of the patient may be displayed.

Figure 8B:
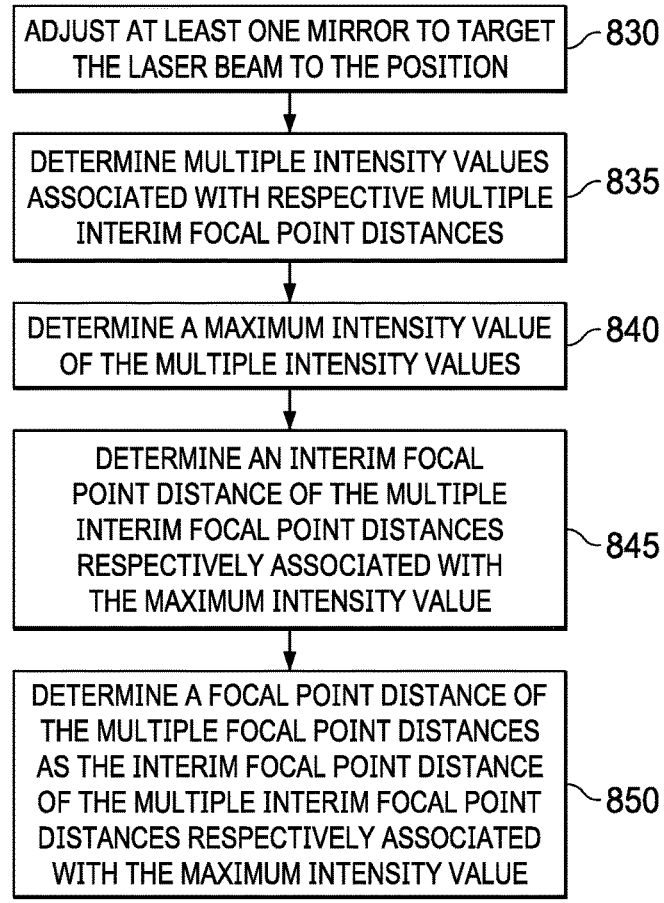
FIG. 8B illustrates an example of method of determining multiple of focal point distances associated with respective multiple positions of a plane orthogonal to a laser beam.

Turning now to FIG. 8B, an example of method of determining multiple of focal point distances associated with respective multiple positions of a plane orthogonal to a laser beam is illustrated. The method illustrated in FIG. 8B may be performed for each position of the multiple positions of the plane orthogonal to the laser beam. In one example, the method illustrated in FIG. 8B may be performed for each position of positions 910A-910M of plane 900. In another example, the method illustrated in FIG. 8B may be performed for each position of some of positions 910A-910M of plane 900.

At 830, at least one mirror may be adjusted to target the laser beam to the position of the multiple positions of the plane orthogonal to the laser beam. The at least one mirror may be adjusted to target the laser beam to any position. As an example, the at least one mirror may be adjusted to target the laser beam to position 910F. Scanner 144 may include one or more mirrors. For example, scanner 144 may target the laser beam to the position of the multiple positions of the plane orthogonal to the laser beam. Scanner 144 may adjust at least one mirror to target the laser beam to the position of the multiple positions of the plane orthogonal to the laser beam.

At 835, multiple intensity values associated with respective interim focal point distances may be determined. In one example, multiple intensity values associated with respective interim focal point distances 950A-950C of laser beam 915, illustrated in respective FIGS. 9R-9T, may be determined. In another example, multiple intensity values associated with respective interim focal point distances 930A-930C, 930E, and 930F of laser beam 915, illustrated in respective FIGS. 9H-9J, 9L and 9M, may be determined. The multiple intensity values associated with the respective interim focal point distances may be determined via a method illustrated in FIG. 8C.

At 840, a maximum intensity value of the multiple intensity values may be determined. In one example, computer system 152 may determine a maximum intensity value of the multiple intensity values. In another example, computer system 430 may determine a maximum intensity value of the multiple intensity values. If a maximum intensity value associated with interim focal point distance 930D has been determined, another maximum intensity value of the multiple intensity values may be determined. For example, the other maximum intensity value of the multiple intensity values may be associated with interim focal point distance 930F. As an example, a maximum intensity value, of the multiple intensity values, associated with interim focal point distance 930F may be determined.

At 845, an interim focal point distance of the multiple interim focal point distances respectively associated with the maximum intensity value may be determined. In one example, interim focal point distance 950C of interim focal point distances 950A-950C may be determined. In another example, interim focal point distance 930F of interim focal point distances 930A-930C, 930E, and 930F may be determined.

At 850, a focal point distance of the multiple focal point distances may be determined as the interim focal point distance of the multiple interim focal point distances respectively associated with the maximum intensity value. In one example, a focal point distance of the multiple focal point distances may be determined as interim focal point distance 950C, of interim focal point distances 950A-950C, respectively associated with the maximum intensity value. In another example, a focal point distance of the multiple focal point distances may be determined as interim focal point distance 930F, of interim focal point distances 930A-930C, 930E, and 930F, respectively associated with the maximum intensity value.

Figure 8C:
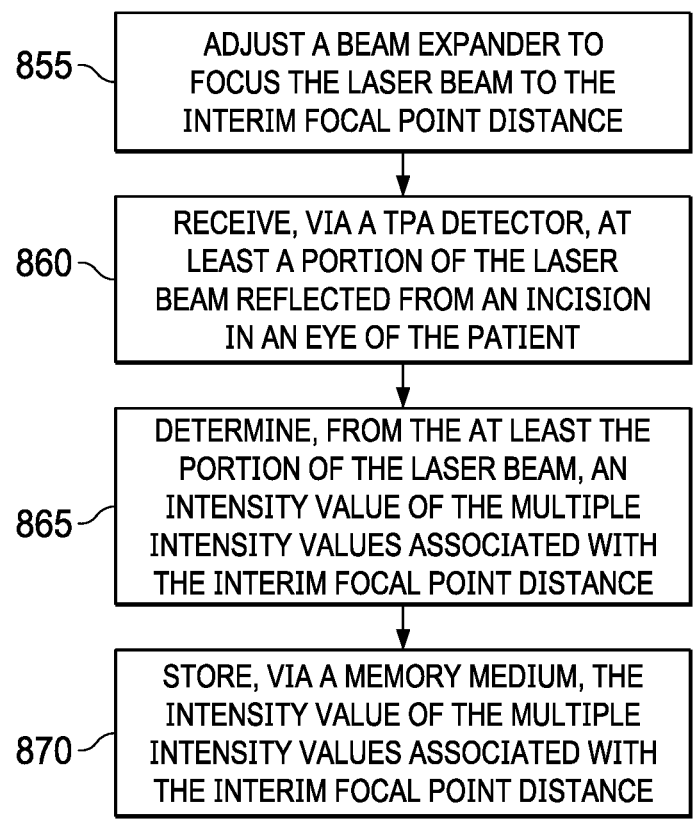
FIG. 8C illustrates an example of a method of determining multiple intensity values associated with respective multiple interim focal point distances.
Figure 9R:
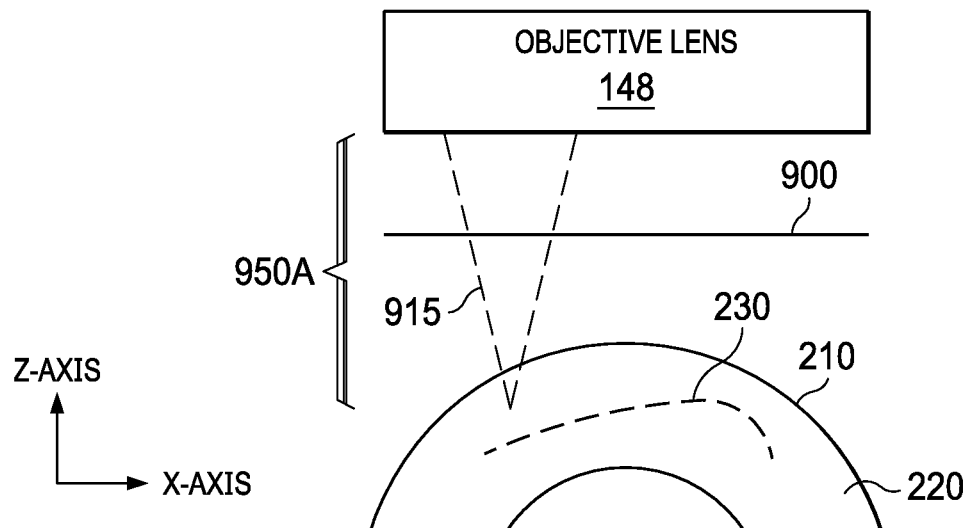
FIGS. 9R-9T illustrate examples of interim focal point distances of a laser beam associated with respective multiple intensity values.
Figure 9S:
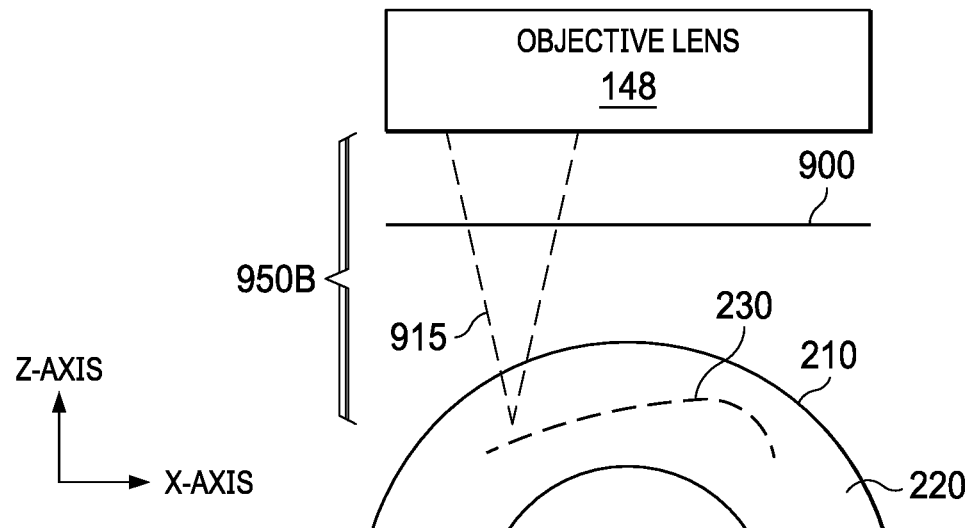
Figure 9T:
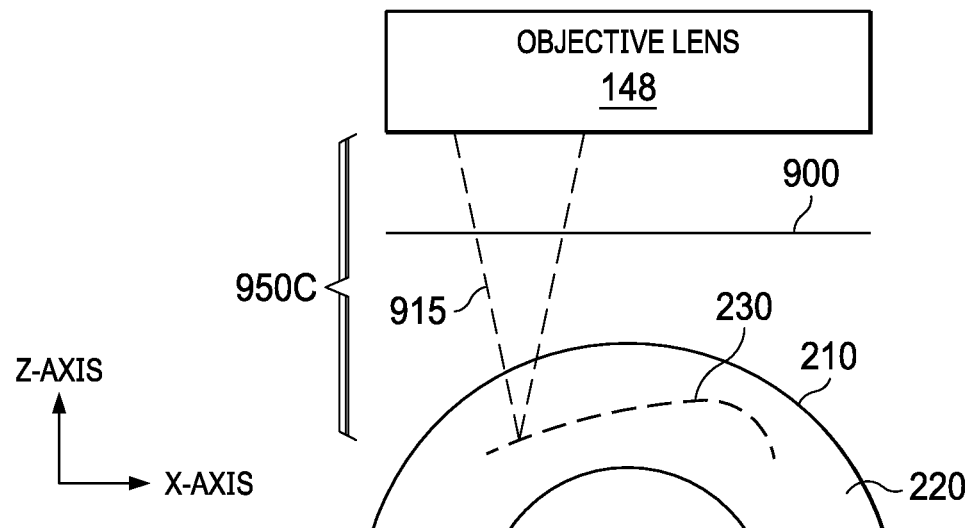
Figure 9U:
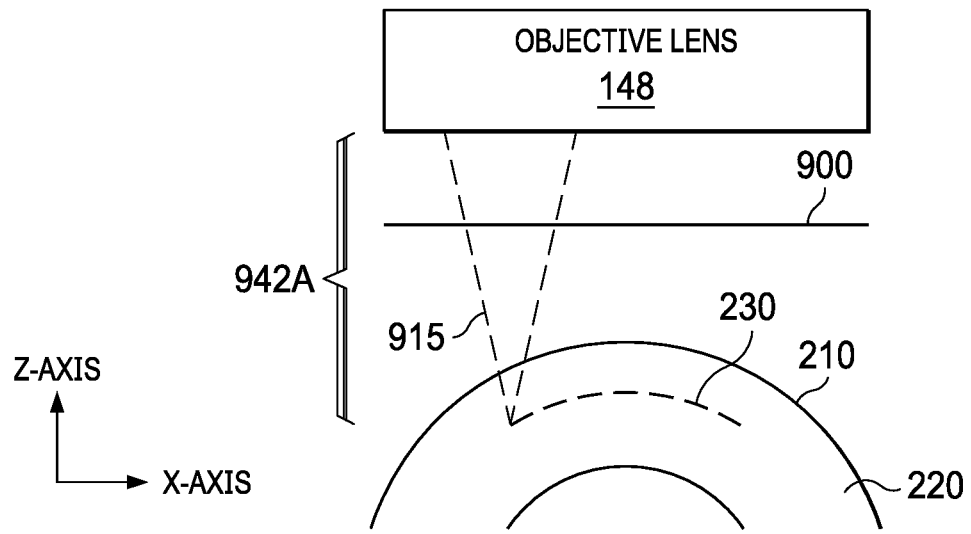
FIGS. 9U-9X illustrate examples of multiple focal point distances of a laser beam.
Figure 9V:
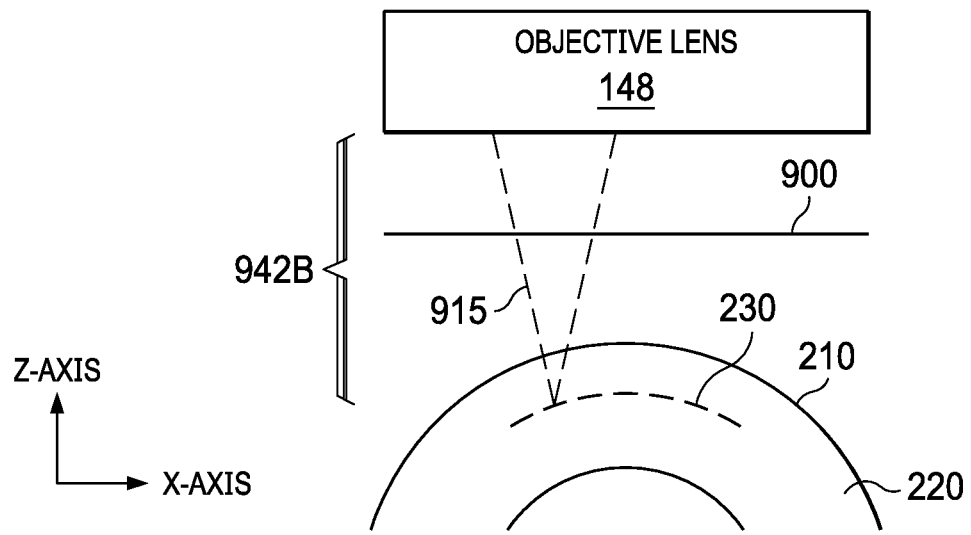
Figure 9W:
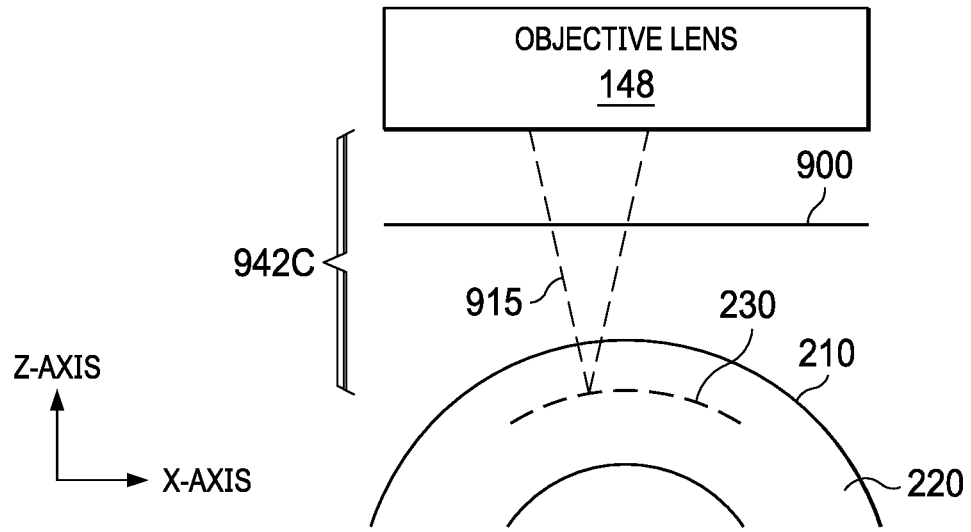
Figure 9X:
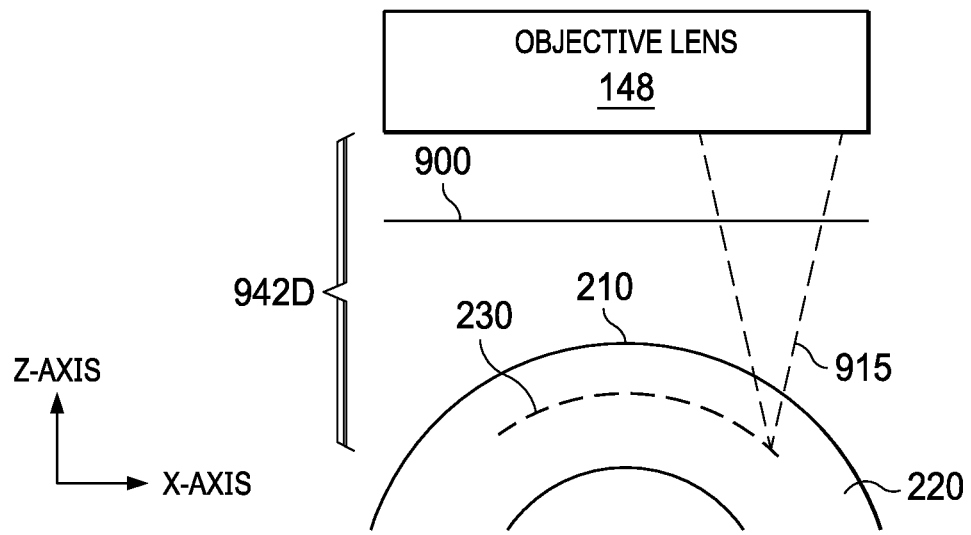

Turning now to FIG. 8C, an example of a method of determining multiple intensity values associated with respective multiple interim focal point distances is illustrated. The method illustrated in FIG. 8C may be performed for each interim focal point distance of the multiple interim focal point distances. For example, the method illustrated in FIG. 8C may be performed for each interim focal point distance of interim focal point distances 950A-950C.

At 855, a beam expander may be adjusted to focus the laser beam to the interim focal point distance. In one example, beam expander 141 may be adjusted to focus the laser beam to interim focal point distance 930. In another example, beam expander 141 may be adjusted to focus the laser beam to interim focal point distance 950. Adjusting beam expander 141 to focus the laser beam to an interim focal point distance may include adjusting one or more lenses of beam expander 141. In one example, one or more of lenses 142A and 142B may be adjusted to focus the laser beam to interim focal point distance 930. In another example, one or more of lenses 142A and 142B may be adjusted to focus the laser beam to interim focal point distance 950.

At 860, at least a portion of the laser beam reflected from an incision in an eye of a patient may be received via a TPA. For example, TPA detector 130 may receive at least a portion of the laser beam reflected from incision 230 in eye 116 of patient 320.

At 865, an intensity value, of the multiple intensity values, associated with the interim focal point distance may be determined from the at least the portion of the laser beam. In one example, an intensity value associated with interim focal point distance 930 may be determined. An intensity value associated with interim focal point distance 930F may be a maximum intensity value. In another example, an intensity value associated with interim focal point distance 950 may be determined. An intensity value associated with interim focal point distance 950C may be a maximum intensity value.

Determining, from the at least the portion of the laser beam, an intensity value of the multiple intensity values associated with the interim focal point distance may include an ADC receiving an analog signal from the TPA detector. Determining, from the at least the portion of the laser beam, an intensity value of the multiple intensity values associated with the interim focal point distance may include the ADC converting the analog signal from the TPA detector to the intensity value of the multiple intensity values associated with the interim focal point distance. In one example, the ADC may convert current into digital values. In another example, the ADC may convert voltage into digital values.

At 870, the intensity value, of the multiple intensity values, associated with the interim focal point distance may be stored via a memory medium. For example, the intensity value associated with the interim focal point distance and the interim focal point distance may be stored via the memory medium. The interim focal point distance may be accessed and/or may be retrieved from the memory medium via the intensity value associated with the interim focal point distance. For example, a focal point distance may be accessed and/or may be retrieved from the memory medium via a maximum intensity value.

Storing the intensity value associated with the interim focal point distance and the interim focal point distance via the memory medium may include storing the intensity value associated with the interim focal point distance and the interim focal point distance via a database. The interim focal point distance may be accessed and/or may be retrieved from the database via the intensity value associated with the interim focal point distance. For example, a focal point distance may be accessed and/or may be retrieved from the database via a maximum intensity value. The database may be stored locally, via a remote computer system, or via a remote data center, among others. In one example, the database may include a relational database. In a second example, the database may include a graph database. In a third example, the database may include an associative array. In another example, the database may include a NoSQL database.

Figure 10L:
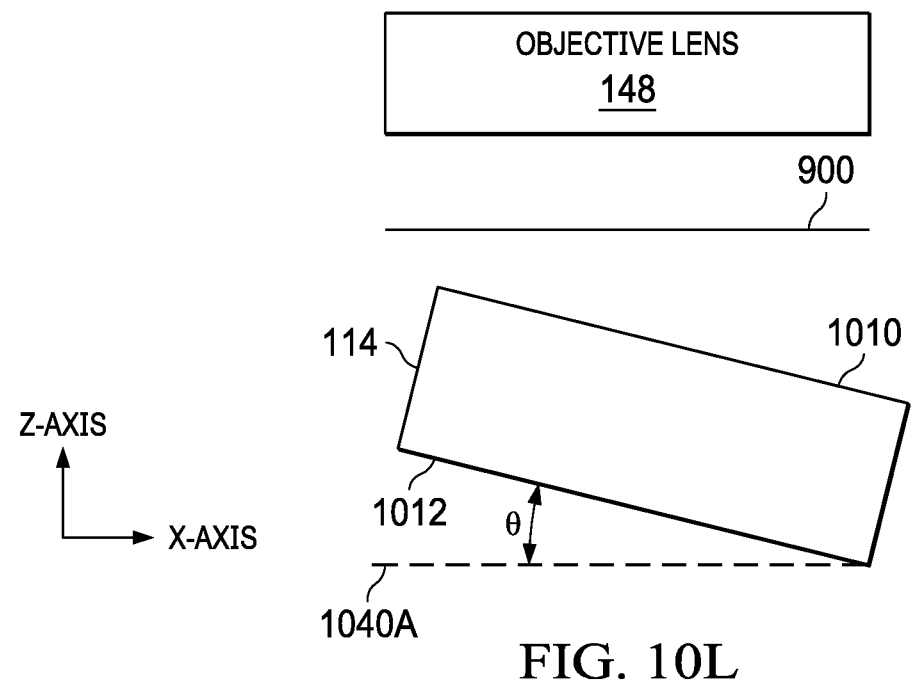
FIGS. 10L and 10M illustrate examples of a patient interface at an angle to plane.
Figure 10M:
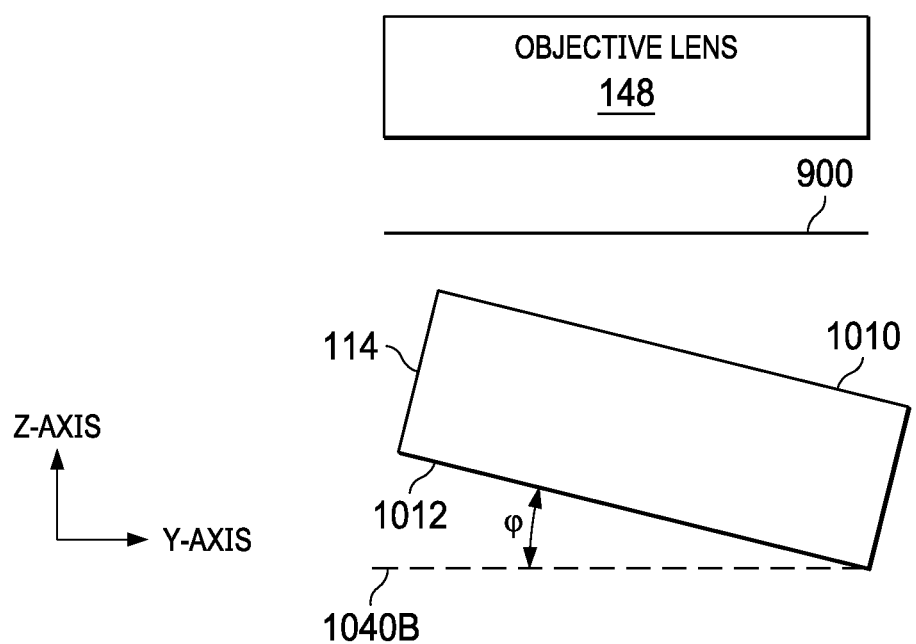

Turning now to FIGS. 10L and 10M, examples of a patient interface at an angle to plane are illustrated. As shown in FIG. 10L, a line 1040A may be parallel to plane 900 and a X-axis. Determining a topography of a surface of a patient interface may include determining an angle θ. As illustrated in FIG. 10M, a line 1040B may be parallel to plane 900 and a Y-axis. For example, line 1040B may be orthogonal to line 1040A. Lines 1040A and 1040B may be parallel to plane 900. Determining a topography of a surface of a patient interface may include determining an angle φ. One or more of angles θ and φ may be utilized in determining and/or maintaining a depth of a cut or incision in eye 116. For example, when eye 116 is in contact with surface 1012 of patient interface 114, one or more of angles θ and φ may be utilized in determining and/or maintaining a depth of a cut or an incision in eye 116.

One or more of the method and/or process elements and/or one or more portions of a method and/or processor elements may be performed in varying orders, may be repeated, or may be omitted. Furthermore, additional, supplementary, and/or duplicated method and/or process elements may be implemented, instantiated, and/or performed as desired. Moreover, one or more of system elements may be omitted and/or additional system elements may be added as desired.

A memory medium may be and/or may include an article of manufacture. For example, the article of manufacture may include and/or may be a software product and/or a program product. The memory medium may be coded and/or encoded with processor-executable instructions in accordance with one or more flowcharts, systems, methods, and/or processes described herein to produce the article of manufacture.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A medical system, comprising:
   at least one processor;
   a laser coupled to the at least one processor and configured to produce a laser beam;
   a detector coupled to the at least one processor and configured to determine an intensity of each portion of a plurality of portions of the laser beam reflected from an incision in an eye of a patient; and
   a memory medium coupled to the at least one processor, the memory medium comprising instructions that, when executed by the at least one processor, cause the medical system to:
   determine a first plurality of focal point distances associated with a respective plurality of positions of a plane orthogonal to the laser beam;
   determine a second plurality of focal point distances associated with the respective plurality of positions of the plane orthogonal to the laser beam, via for each position of the plurality of positions, the instructions further cause the medical system to:
   target the laser beam to the position;
   determine, according to the plurality of portions of the laser beam, a plurality of intensity values associated with a respective plurality of interim focal point distances, each interim focal point distance greater than each focal point distance of the first plurality of focal point distances associated with the position of the plurality of positions;

determine a maximum intensity value of the plurality of intensity values associated with the respective plurality of interim focal point distances;

determine an interim focal point distance of the plurality of interim focal point distances respectively associated with the maximum intensity value;

determine a focal point distance of the plurality of focal point distances as the interim focal point distance of the plurality of interim focal point distances respectively associated with the maximum intensity value; and determine a depth of the incision in the eye of the patient based at least on differences between each of the second plurality of focal point distances and each respective one of the first plurality of focal point distances.

2. The medical system of claim 1, wherein, to determine the plurality of intensity values associated with the respective plurality of interim focal point distances, the instructions further cause the medical system to, for each interim focal point distance of the plurality of interim focal point distances:

focus the laser beam at the interim focal point distance;

receive, via the detector, a portion of the plurality of portions of the laser beam reflected from the incision in the eye of the patient; and determine, from the portion, an intensity value of the plurality of intensity values associated with the interim focal point distance.

3. The medical system of claim 2, wherein, to determine, from the portion, the intensity value of the plurality of intensity values associated with the interim focal point distance, the instructions further cause the medical system to:

receive, by an analog to digital converter (ADC), an analog signal from the detector; and convert, by the ADC, the analog signal from the detector to the intensity value of the plurality of intensity values associated with the interim focal point distance.

4. The medical system of claim 1, wherein the detector is a two-photon absorption (TPA) detector.

5. The medical system of claim 1, wherein the instructions further cause the medical system to:

determine a topography of the incision in the eye of the patient based at least on differences between each of the second plurality of focal point distances and each respective one of the first plurality of focal point distances.

6. The medical system of claim 1, wherein the instructions further cause the medical system to:

determine a flap thickness according to the depth of at least one incision in the eye.

7. The medical system of claim 1, wherein the instructions further cause the medical system to:

correct a cutting depth according to the depth of at least one incision in the eye.

8. The medical system of claim 1, wherein the instructions further cause the medical system to:

display the depth of at least one incision in the eye of the patient.

9. A method of operating a medical system, comprising:

determining a first plurality of focal point distances associated with a respective plurality of positions of a plane orthogonal to a laser beam;

determining a second plurality of focal point distances associated with the respective plurality of positions of the plane orthogonal to the laser beam by, for each position of the plurality of positions:

targeting the laser beam to the position;

determining, according to a plurality of portions of the laser beam reflected from an incision in an eye of a patient, a plurality of intensity values associated with a respective plurality of interim focal point distances, each interim focal point distance greater than each focal point distance of the first plurality of focal point distances associated with the position of the plurality of positions;

determining a maximum intensity value of the plurality of intensity values associated with the respective plurality of interim focal point distances;

determining an interim focal point distance of the plurality of interim focal point distances respectively associated with the maximum intensity value;

determining a focal point distance of the plurality of focal point distances as the interim focal point distance of the plurality of interim focal point distances respectively associated with the maximum intensity value; and determining a depth of the incision in the eye of the patient based at least on differences between each of the second plurality of focal point distances and each respective one of the first plurality of focal point distances.

10. The method of claim 9, further comprising determining the plurality of intensity values associated with the respective plurality of interim focal point distances by, for each interim focal point distance of the plurality of interim focal point distances:

focusing the laser beam at the interim focal point distance;

receiving, via a detector, a portion of the plurality of portions of the laser beam reflected from the incision in the eye of the patient; and determining from the portion, an intensity value of the plurality of intensity values associated with the interim focal point distance.

11. The method of claim 10, further comprising determining, from the portion, the intensity value of the plurality of intensity values associated with the interim focal point distance by:

receiving an analog signal from the detector; and converting the analog signal from the detector to the intensity value of the plurality of intensity values associated with the interim focal point distance.

12. The method of claim 9, further comprising:

determining a topography of the incision in the eye of the patient based at least on differences between each of the second plurality of focal point distances and each respective one of the first plurality of focal point distances.

13. The method of claim 9, further comprising:

determining a flap thickness according to the depth of at least one incision in the eye.

14. The method of claim 9, further comprising:

correcting a cutting depth according to the depth of at least one incision in the eye.

15. The method of claim 9, further comprising:

displaying the depth of at least one incision in the eye of the patient.

* * * * *